(12) United States Patent
Joung et al.

(10) Patent No.: US 10,676,749 B2
(45) Date of Patent: *Jun. 9, 2020

(54) TALE TRANSCRIPTIONAL ACTIVATORS

(71) Applicant: The General Hospital Corporation, Boston, MA (US)

(72) Inventors: J. Keith Joung, Winchester, MA (US); Morgan Maeder, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/766,713

(22) PCT Filed: Feb. 7, 2014

(86) PCT No.: PCT/US2014/015343
§ 371 (c)(1),
(2) Date: Aug. 7, 2015

(87) PCT Pub. No.: WO2014/124284
PCT Pub. Date: Aug. 14, 2014

(65) Prior Publication Data
US 2015/0376626 A1 Dec. 31, 2015

Related U.S. Application Data

(60) Provisional application No. 61/762,125, filed on Feb. 7, 2013.

(51) Int. Cl.
| | | |
|---|---|---|
| *C07K 14/195* | (2006.01) |
| *C12N 15/67* | (2006.01) |
| *C07K 14/435* | (2006.01) |
| *C07K 14/005* | (2006.01) |
| *C07K 14/47* | (2006.01) |
| *C12N 15/63* | (2006.01) |
| *G16B 20/00* | (2019.01) |
| *G01N 33/53* | (2006.01) |

(52) U.S. Cl.
CPC .......... *C12N 15/635* (2013.01); *C07K 14/005* (2013.01); *C07K 14/195* (2013.01); *C07K 14/435* (2013.01); *C07K 14/4702* (2013.01); *C12N 15/67* (2013.01); *G01N 33/5308* (2013.01); *G16B 20/00* (2019.02); *C07K 2319/71* (2013.01); *C07K 2319/80* (2013.01); *C12N 2710/16622* (2013.01)

(58) Field of Classification Search
CPC .......... C07K 2319/80; C07K 2319/71
See application file for complete search history.

(56) References Cited

U.S. PATENT DOCUMENTS

| | | | |
|---|---|---|---|
| 4,603,044 A | 7/1986 | Geho et al. |
| 4,797,368 A | 1/1989 | Carter et al. |
| 4,957,773 A | 9/1990 | Spencer et al. |
| 6,007,988 A | 12/1999 | Choo et al. |
| 6,013,453 A | 1/2000 | Choo et al. |
| 6,453,242 B1 | 9/2002 | Eisenberg et al. |
| 6,492,117 B1 | 12/2002 | Choo et al. |
| 6,503,717 B2 | 1/2003 | Case et al. |
| 6,511,808 B2 | 1/2003 | Wolffe et al. |
| 6,534,261 B1 | 3/2003 | Cox, III et al. |
| 7,001,768 B2 | 2/2006 | Wolfe et al. |
| 7,220,719 B2 | 5/2007 | Case |
| 7,741,086 B2 | 6/2010 | Shi |
| 7,914,796 B2 | 3/2011 | Miller et al. |
| 8,034,598 B2 | 10/2011 | Miller |
| 8,071,370 B2 | 12/2011 | Wolffe |
| 8,771,986 B2 | 7/2014 | Miller |
| 8,962,281 B2 | 2/2015 | Doyon |
| 10,273,271 B2 | 4/2019 | Joung et al. |
| 2002/0160940 A1 | 1/2002 | Case et al. |
| 2002/0106680 A1 | 8/2002 | Shinmyo |
| 2002/0119498 A1 | 8/2002 | Joung et al. |
| 2002/0164575 A1 | 11/2002 | Case et al. |
| 2003/0083283 A1 | 5/2003 | Bennett et al. |
| 2006/0115850 A1 | 6/2006 | Schatz |
| 2008/0131962 A1 | 6/2008 | Miller |
| 2009/0133158 A1 | 5/2009 | Lahaye et al. |
| 2010/0132069 A1 | 5/2010 | Lahaye et al. |
| 2011/0059502 A1 | 3/2011 | Chalasani |
| 2011/0112040 A1 | 5/2011 | Liu et al. |
| 2011/0301073 A1* | 12/2011 | Gregory ................ C12N 15/62 514/1.1 |
| 2012/0064620 A1 | 3/2012 | Bonas |
| 2012/0100569 A1 | 4/2012 | Liu et al. |
| 2013/0323220 A1 | 12/2013 | Joung et al. |

(Continued)

FOREIGN PATENT DOCUMENTS

| | | |
|---|---|---|
| EP | 1941060 | 7/2008 |
| EP | 2206723 | 7/2010 |

(Continued)

OTHER PUBLICATIONS

Sera et al. Zinc-finger-based artificial transcription factors and their applications. Advanced Drug Delivery Reviews, vol. 61, pp. 513-526, Apr. 2009.*

Supporting text, printed as pages 1/8-8/8, 5 pages. of supplemental figures, and one page of supplemental table for Geißler et al. Transcriptional activators of human genes with programmable DNA-specificity. PLoS One, vol. 6, e19509, 2011. (Year: 2011).*

Akopian et al., "Chimeric recombinases with designed DNA sequence recognition," Proc Natl Acad Sci USA, Jul. 22, 2003;100(15):8688-91.

Alvarez and Curiel, "A phase I study of recombinant adenovirus vector-mediated intraperitoneal delivery of herpes simplex virus thymidine kinase (HSV-TK) gene and intravenous ganciclovir for previously treated ovarian and extraovarian cancer patients," Hum. Gene Ther., Mar. 1997, 5:597-613.

(Continued)

*Primary Examiner* — Jennifer Dunston
(74) *Attorney, Agent, or Firm* — Fish & Richardson P.C.

(57) ABSTRACT

Computer programs, algorithms, and methods for identifying TALE-activator binding sites, and methods for generation and use of TALE-activators that bind to these sites.

20 Claims, 8 Drawing Sheets

Specification includes a Sequence Listing.

(56) References Cited

U.S. PATENT DOCUMENTS

| | | | |
|---|---|---|---|
| 2014/0274812 | A1 | 9/2014 | Joung et al. |
| 2015/0267176 | A1 | 9/2015 | Joung et al. |
| 2016/0010076 | A1 | 1/2016 | Joung et al. |
| 2016/0024523 | A1 | 1/2016 | Joung et al. |

FOREIGN PATENT DOCUMENTS

| | | | | |
|---|---|---|---|---|
| JP | 2003-501069 | | 1/2003 | |
| JP | 2003-531616 | | 10/2003 | |
| JP | 2013-529083 | | 7/2013 | |
| JP | 2015-527889 | | 9/2015 | |
| WO | WO 1991/016024 | | 10/1991 | |
| WO | WO 1991/017424 | | 11/1991 | |
| WO | WO 9319202 | | 9/1993 | |
| WO | WO 1993/024641 | | 12/1993 | |
| WO | WO 9517413 | | 6/1995 | |
| WO | WO 9810095 | | 3/1998 | |
| WO | WO 9947536 | | 9/1999 | |
| WO | WO 00/75368 | | 12/2000 | |
| WO | WO 2001/019981 | | 3/2001 | |
| WO | WO 2001/053480 | | 7/2001 | |
| WO | WO 0183732 | | 11/2001 | |
| WO | WO 0183732 | A2 * | 11/2001 | ......... C07K 14/4702 |
| WO | WO 2002/057308 | | 7/2002 | |
| WO | WO 2002/099084 | | 12/2002 | |
| WO | WO 2004/099366 | | 11/2004 | |
| WO | WO 2006/071608 | | 7/2006 | |
| WO | WO 2007/128982 | | 11/2007 | |
| WO | WO 2009/134409 | | 11/2009 | |
| WO | WO 2010/037001 | | 4/2010 | |
| WO | WO 2010/079430 | | 7/2010 | |
| WO | WO 2011/017293 | | 2/2011 | |
| WO | WO 2011/019385 | | 2/2011 | |
| WO | WO 2011/072246 | | 6/2011 | |
| WO | WO 2011/146121 | | 11/2011 | |
| WO | WO 2012/138939 | | 10/2012 | |
| WO | WO 2013/012674 | | 1/2013 | |
| WO | WO 2013/017950 | | 2/2013 | |

OTHER PUBLICATIONS

Arora et al., "Residues 1-254 of anthrax toxin lethal factor are sufficient to cause cellular uptake of fused polypeptides," J. Biol. Chem., Feb. 1993, 268:3334-41.

Aslanidis et al., "Ligation-independent cloning of PCR products (LIC-PCR)," Nucleic Acids Res., Oct. 25, 1990;18(20):6069-74.

Australian Office Action in Australian Application No. 2012284365, dated Jul. 29, 2016, 5 pages.

Bannister et al., "Histone methylation: Dynamic or static?," Cell, Jun. 28, 2002, 109(7): 801-806.

Batt, C.A., Chapter 14. Genetic Engineering of Food Proteins in Food Proteins and Their Applications, Damodaran, S., Ed. CRC Press, Mar. 12, 1997, p. 425.

Bello et al., "Hypermethylation of the DNA repair gene MGMT: association with TP53 G:C to A:T transitions in a series of 469 nervous system tumors," Mutat. Res., Oct. 2004, 554:23-32.

Bergmann et al., "Epigenetic engineering shows H3K4me2 is required for HJURP targeting and CENP-A assembly on a synthetic human kinetochore," The EMBO Journal, vol. 30, pp. 328-340, Jan. 2011, published online Dec. 14, 2010, including pp. 1/14-14/14 of Supplementary Data.

Bibikova et al., "Enhancing gene targeting with designed zinc finger nucleases," Science, May 2, 2003;300(5620):764.

Bibikova et al., "Stimulation of homologous recombination through targeted cleavage by chimeric nucleases," Mol Cell Biol., Jan. 2001;21(1):289-97.

Blaese et al., "T lymphocyte-directed gene therapy for ADA-SCID: initial trial results after 4 years," Science, Oct. 1995, 270(5235):475-480.

Bonar et al., "Genetic and Structural Characterization of the Avirulence Gene AVR-BS3 From Xanthomonas-Campestris Pathovar Vesicatoria," Molecular and General Genetics, Jul. 1989, 218(1): 127-136.

Briggs et al., "Iterative capped assembly: rapid and scalable synthesis of repeat-module DNA such as TAL effectors from individual monomers," Nucleic Acids Res., Aug. 2012;40(15):e117.

Burnett et al., "Conditional macrophage ablation in transgenic mice expressing a Fas-based suicide gene," J. Leukoc. Biol., Apr. 2004, 75(4):612-623.

Cade et al., "Highly efficient generation of heritable zebrafish gene mutations using homo- and heterodimeric TALENs," Nucleic Acids Res., Sep. 2012, 40(16):8001-10.

Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.

Caron et al., ""Intracellular Delivery of a Tat-eGFP Fusion Protein into Muscle Cells,"" Mol Ther., Mar. 2001, 3:310-318.

Castellano et al., "Inducible recruitment of Cdc42 or WASP to a cell-surface receptor triggers actin polymerization and filopodium formation," Curr. Biol., 1999, 9(7): 351-360.

Chim et al., "Methylation profiling in multiple myeloma," Leuk. Res., Apr. 2004, 28:379-85.

Coffman et al., "Improved renal function in mouse kidney allografts lacking MHC class I antigens," J. Immunol., Jul. 1993, 151:425-35.

Costa et al., "REELIN and schizophrenia: a disease at the interface of the genome and the epigenome," Mol. Interv., Feb. 2002, 2:47-57.

Crabtree and Schreiber, "Three-part inventions: intracellular signaling and induced proximity," Trends Biochem. Sci., Nov. 1996, 21(11):418-422.

Cronican et al., "A Class of Human Proteins that Deliver Functional Proteins into Mammalian Cells In Vitro and In Vivo," Chem Biol., Jul. 2011, 18:833-838.

Cronican et al., "Potent Delivery of Functional Proteins into Mammalian Cells in Vitro and in Vivo Using a Supercharged Protein," ACS Chem. Biol., 2010, 5:747.

Davis, "Transcriptional regulation by MAP kinases," Mol Reprod Dev., Dec. 1995;42(4):459-67.

De Zhu, "The altered DNA methylation pattern and its implications in liver cancer," Cell. Res., 2005, 15:272-80.

Derossi et al., "The Third Helix of the Antennapedia Homeodornain Translocates through Biological Membranes," J. Biol. Chem., Apr. 1994, 269:10444.

Deshayes et al., "Cell-penetrating peptides: tools for intracellular delivery of therapeutics," Cell. Mol. Life Sci., Aug. 2005, 62:1839-49.

Donnelly et al., "Targeted delivery of peptide epitopes to class I major histocompatibility molecules by a modified Pseudomonas exotoxin," PNAS, Apr. 1993, 90:3530-34.

Doyon et al., "Heritable targeted gene disruption in zebrafish using designed zinc-finger nucleases," Nat Biotechnol., Jun. 2008, 26:702-708.

Dranoff et al., "A phase I study of vaccination with autologous, irradiated melanoma cells engineered to secrete human granulocyte-macrophage colony stimulating factor," Hum. Gene Ther., Jan. 1997, 8(1):111-23.

Dunbar et al., ""Retrovirally Marked CD34-Enriched Peripheral Blood and Bone Marrow Cells Contribute to Long-Term Engraftment After Autologous Transplantation,"" Blood, Jun. 1995, 85:3048-3057.

El-Andaloussi et al., "Cell-penetrating peptides: mechanisms and applications," Curr. Pharm. Des., 2005, 11:3597-3611.

Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.

Endoh et al., "Cellular siRNA delivery using TatU1A and photo-induced RNA interference," Methods Mol. Biol., 2010, 623:271-281.

Entry for CDKN2A, cyclin-dependent kinase inhibitor 2A [Homo sapiens (human)], Gene ID: 1029, updated on Oct. 31, 2016, and printed from http:www.ncbi.nlm nih.gov/gene/1029 as pp. 1/9 on Nov. 1, 2016.

Esteller et al., "A Gene Hypermethylation Profile of Human Cancer," Cancer Res., Apr. 2001, 61:3225-9.

(56) References Cited

OTHER PUBLICATIONS

Esteller et al., "Promoter Hypermethylation and BRCA1 Inactivation in Sporadic Breast and Ovarian Tumors," J. Natl. Cancer Inst., Apr. 2000, 92:564-9.
European Office Action in European Application No. 13845212, dated May 18, 2016, 1 page.
Evans et al., Binding, Regeneration of Plants, Plant Protoplasts, pp. 21-73 (1985).
Evans et al., Protoplasts Isolation and Culture, Handbook of Plant Cell Culture, pp. 124-176 (1983).
Extended European Search Report in European Application No. 12814750.1, dated Jun. 30, 2015,13 pages.
Extended European Search Report in European Application No. 13797024, dated Mar. 15, 2016, 9 pages.
Extended European Search Report in European Application No. 13845212, dated Apr. 29, 2016, 6 pages.
Externded European Search Report in European Application No. 14749683, dated Sep. 9, 2016, 7 pages.
Foley et al., "Targeted mutagenesis in zebrafish using customized zinc-finger nucleases", Nature Protocols, Nature Publishing Group, Jan. 2009, 4(12):1855-1868.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Futaki, "Oligoarginine vectors for intracellular delivery: design and cellular-uptake mechanisms," Biopolymers, 2006, 84:241-249.
Gao et al., "Hypermethylation of the RASSF1A gene in gliomas," Clin. Chim. Acta., Nov. 2004, 349:173-9.
Gavin et al., "Dimethylated lysine 9 of histone 3 is elevated in schizophrenia and exhibits a divergent response to histone deacetylase inhibitors in lymphocyte cultures," J. Psychiatry Neurosci., May 2009, 34(3):232-7.
Gong and Zhu, "Active DNA demethylation by oxidation and repair," Cell Research, 2011, 21:1649-1651.
Graef et al., "Proximity and orientation underlie signaling by the non-receptor tyrosine kinase ZAP70," EMBO. J., 1997, 16(18):5618-5628.
Gregory et al., "Selective DNA demethylation by fusion of TOG with a sequence-specific DNA-binding domain", Epigenetics, Apr. 2012, 7(4):344-349.
Gross and Garrard, "Nuclease Hypersensitive Sites in Chromatin," Annu. Rev. Biochem., Jul. 1988, 57:159-97.
Gu et al., "R gene expression induced by a type-III effector triggers disease resistance in rice," Nature, Jun. 23, 2005;435(7045):1122-5.
Hakimi et al., "A core-BRAF35 complex containing histone deacetylase mediates repression of neuronal-specific genes," Proceedings of the National Academy of Sciences of the United States of America, May 28, 2002, 99(11): 7420-7425.
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviml targeting of human breast cancer cells," PNAS, Oct. 1995, 92:9747-51.
Heppard et al., "Developmental and Growth Temperature Regulation of Two Different Microsomal [omega]-6 Desaturase Genes in Soybeans," Plant Physiol., 1996, 110:311-319.
Hermonat & Muzyczka, "Use of adeno-associated virus as a mammalian DNA cloning vector: Transduction of neomycin resistance into mammalian tissue culture cells," PNAS, Oct. 1984, 81:6466-70.
Hopp et al., "A Short Polypeptide Marker Sequence Useful for Recombinant Protein Identification and Purification," BioTechnology, Oct. 1988, 6:1204-10.
Huang Shi, "Histone methyltransferases, diet nutrients and tumour suppressors," Nature Reviews. Cancer, Jun. 2002, 2(6): 469-7-476.
Humphrey et al., "Stable histone deacetylase complexes distinguished by the presence of SANT domain proteins CoREST/kiaa0071 and Mta-L1," Journal of Biological Chemistry, Mar. 2, 2001, 276(9): 6817-6824.

International Preliminary Report on Patentability in International Application No. PCT/US2012/046451, dated Jan. 21, 2014, 6 pages.
International Preliminary Report on Patentability in International Application No. PCT/US2013/043075, dated Dec. 2, 2014, 7 pages.
International Preliminary Report on Patentability in International Application No. PCT/US2013/064511, dated Apr. 23, 2015, 12 pages.
International Search Report and Written Opinion in International Application No. PCT/US2012/046451, dated Nov. 15, 2012, 8 pages.
International Search Report and Written Opinion in International Application No. PCT/US2013/043075, dated Sep. 26, 2013, 10 pages.
International Search Report and Written Opinion in International Application No. PCT/US2013/064511, dated Jan. 30, 2014, 8 pages.
Japanese Office Action in Japanese Application No. 2014-520317, dated Apr. 5, 2016, 8 pages (with English translation).
Joung et al., "Reply to "Successful genome editing with modularly assembled zinc finger nucleases"," Nat. Methods, Jan. 2010, 7:91-92.
Joung et al., "A bacterial two-hybrid selection system for studying protein-DNA and protein-protein interactions," Proc Natl Acad Sci USA, Jun. 20, 2000;97(13):7382-7.
Kay et al., "A bacterial effector acts as a plant transcription factor and induces a cell size regulator," Science, Oct. 26, 2007;318(5850):648-51.
Kearns et al., "Recombinant adeno-associated virus (AAV-CFTR) vectors do not integrate in a site-specific fashion in an immortalized epithelial cell line," Gene Ther., Sep. 1996, 9:748-55.
Kim et al., "Hybrid restriction enzymes: zinc finger fusions to Fok I cleavage domain," Proc Natl Acad Sci USA, Feb. 6, 1996;93(3):1156-60.
Klee et al., "Agrobacterium-Mediated Plant Transformation and its Further Applications to Plant Biology," Ann. Rev. Plant Phys., Jun. 1987, 38:467-486.
Klimpel et al., "Anthrax toxin protective antigen is activated by a cell surface protease with the sequence specificity and catalytic properties of furin," PNAS, Nov. 1992, 89:10277-81.
Ko et al., "Impaired hydroxylation of 5-methylcytosine in myeloid cancers with mutant TET2," Nature, Dec. 2010, 468(7325):839-843.
Kohn et al., "Engraftment of gene-modified umbilical cord blood cells in neonates with adenosine deaminase deficiency," Nat. Med., 1995, 1:1017-1023.
Koller et al., "Normal development of mice deficient in beta 2M, MHC class I proteins, and CD8+ T cells," Science, Jun. 1990, 248:1227-30.
Kondo et al., "Epigenetic changes in colorectal cancer," Cancer Metastasis Reviews, Jan. 2004, 23(1-2): 29-39.
Kurmasheva et al., "Upstream CpG island methylation of the PAX3 gene in human rhabdomyosarcomas," Pediatr. Blood Cancer, Apr. 2005, 44:328-37.
Lawrence et al., "Supercharging Proteins Can Impart Unusual Resilience," J. Am. Chem. Soc., 2007, 129:10110-10112.
Lea et al., "Aberrant p16 methylation is a biomarker for tobacco exposure in cervical squamous cell carcinogenesis," Am. J. Obstet. Gynecol., 2004, 190:674-9.
Li et al., "DNA methylation in prostate cancer," Biochim. Biophys. Acta., Sep. 2004, 1704:87-102.
Lin et al., "Inhibition of Nuclear Translocation of Transcription Factor NF-κB by a Synthetic Peptide Containing a Cell Membrane-permeable Motif and Nuclear Localization Sequence," J. Biol. Chem., 1995, 270:14255-58.
Loenarz and Schofield, Oxygenase Catalyzed 5-Methylcytosine Hydroxylation, Chemistry & Biology, Jun. 2009, 16:580-583.
Lund et al., "DNA Methylation Polymorphisms Precede Any Histological Sign of Atherosclerosis in Mice Lacking Apolipoprotein E," J. Biol. Chem., Jul. 2004, 279:29147-54.
Lutz-Freyerinuth et al., "Quantitative determination that one of two potential RNA-binding domains of the A protein component of the U1 small nuclear ribonucleoprotein complex binds with high affinity to stem-loop II of U1 RNA," PNAS, Aug. 1990, 87:6393-97.

(56) References Cited

OTHER PUBLICATIONS

Maeder et al., "Oligomerized pool engineering (OPEN): an 'open-source' protocol for making customized zinc-finger arrays," Nat Protoc., 2009;4(10):1471-501.

Malech et al., "Prolonged production of NADPH oxidase-corrected granulocytes after gene therapy of chronic granulomatous disease," PNAS, Oct. 1997, 94:12133-38.

Mancini et al. "CpG methylation within the 5' regulatory region of the BRCA1 gene is tumor specific and includes a putative CREB binding site," Oncogene, 1998, 16:1161-9.

Mandecki et al., "A totally synthetic plasmid for general cloning, gene expression and mutagenesis in *Escherichia coli*," Gene, Sep. 28, 1990, 94(1):103-107.

Markmann et al., "Indefinite survival of MHC class I-deficient murine pancreatic islet allografts," Transplantation, Dec. 1992, 54:1085-89.

Martin et al., "GAP domains responsible for ras p21-dependent inhibition of muscarinic atrial K+ channel currents," Science, Jan. 1992, 255:192-194.

McNaughton et al., ""Mammalian cell penetration, siRNA transfection, and DNA transfection by supercharged proteins,"" PNAS, Apr. 2009, 106:6111.

Moore et al., "Design of polyzinc finger peptides with structured linkers," Proc Natl Acad Sci USA, Feb. 2001, 98:1432-1436.

Moore et al., "Improved somatic mutagenesis in zebrafish using transcription activator-like effector nucleases (TALENs)," PLoS One., 2012;7(5):e37877, 9 pages.

Mussolino et al., "A novel TALE nuclease scaffold enables high genome editing activity in combination with low toxicity," Nucleic Acids Res., 2011, 39:9283-93.

Muthuswamy et al., "Controlled Dimerization of ErbB Receptors Provides Evidence for Differential Signaling by Homo- and Heterodimers," Mol. Cell. Biol., Oct. 1999, 19(10):6845-6857.

Novak et al., "Functional Characterization of Protease-treated Bacillus anthracia Protective Antigen," J. Biol. Chem., Aug. 1992, 267:17186-93.

Orlando et al., "Zinc-finger nuclease-driven targeted integration into mammalian genomes using donors with limited chromosomal homology," Nucleic Acids Res., Aug. 2010;38(15):e152, 15 pages.

Ovchinnikov et al., "PspXI, a novel restriction endonuclease that recognizes the unusual DNA sequence 5-VCTCGAGB-3," Bulletin of Biotechnology and Physico-chemical Biology, 2005, 1(1):18-24.

Paik W K et al., "Enzymatic Demethylation of Calf Thymus Histones," Biochemical and Biophysical Research Communications, 1973, 51(3): 781-788.

Perelle et al., "Characterization of Clostridium perfringens Iota-Toxin Genes and Expression in *Eschenichia coli*," Infect. Immun., Dec. 1993, 61:5147-56.

Perez-Quintero et al., "An Improved Method for TAL Effectors DNA-Binding Sites Prediction Reveals Functional Convergence in TAL Repertoires of Xanthomonas oryzae Strains," Jul. 2013, Plos One, 8.

Porteus & Baltimore, "Chimeric nucleases stimulate gene targeting in human cells," Science. May 2, 2003;300(5620):763.

Prochiantz, "Getting hydrophilic compounds into cells: lessons from homeopeptides," Curr. Opin. Neurobiol., Oct. 1996, 6:629-634.

Rivenbank et al., "Epigenetic reprogramming of cancer cells via targeted DNA methylation," Epigenetics, Apr. 2012, 7(4): 350-360.

Romer et al., "Plant pathogen recognition mediated by promoter activation of the pepper Bs3 resistance gene," Science, Oct. 26, 2007;318(5850):645-8.

Rosenecker et al., "Adenovirus infection in cystic fibrosis patients: implications for the use of adenoviral vectors for gene transfer," Infection, 1996, 24(1)5-8.

Ruben et al., "Isolation of a rel-related human cDNA that potentially encodes the 65-κD subunit of NF-kappa B," Science, Mar. 1991, 251:1490-93.

Sadowski et al., "GAL4-VP16 is an unusually potent transcriptional activator," Nature, Oct. 1988, 335:563-564.

Samulski et al., "Helper-Free Stocks of Recombinant Adeno-Associated Viruses: Normal Integration Does Not Require Viral Gene Expression," J. Virol., Sep. 1989, 63:3822-28.

Schmidt et al., "Arginine-rich cell-penetrating peptides," FEBS Lett., May 2010, 584:1806-13.

Schonthal, "Regulation of gene expression by serine/threonine protein phosphatases," Semin Cancer Biol., Aug. 1995;6(4):239-48.

Schornack et al., "Gene-for-gene-mediated recognition of nuclear-targeted AvrBs3-like bacterial effector proteins," J Plant Physiol., Feb. 2006;163(3):256-72.

Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.

Sharma, "Schizophrenia, epigenetics and ligand-activated nuclear receptors: a framework for chromatin therapeutics," Schizophr. Res., Jan. 2005, 72:79-90.

Shi et al., "Metabolic enzymes and coenzymes in transcription—a direct link between metabolism and transcription?," Trends in Genetics: TIG, Sep. 2004, 20(9): 445-452.

Skinner et al., "Use of the Glu-Glu-Phe C-terminal epitope for rapid purification of the catalytic domain of normal and mutant ras GTPase-activating proteins," J. Biol. Chem., 1991, 266:14163-14166.

Stenmark et al., "Peptides fused to the amino-terminal end of diphtheria toxin are translocated to the cytosol," J. Cell Biol., Jun. 1991, 113:1025-32.

Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.

Sugio et al., "Two type III effector genes of *Xanthomonas oryzae* pv. oryzae control the induction of the host genes OsTFIIAgamma1 and OsTFX1 during bacterial blight of rice," Proc Natl Acad Sci USA, Jun. 19, 2007;104(25):10720-5.

Szyf et al., "DNA methylation and breast cancer," Biochem. Pharmacol., Sep. 2004, 68:1187-97.

Thiesen et al., "Conserved KRAB protein domain identified upstream from the zinc finger region of Kox 8," Nucleic Acids Res., 1991, 19:3996.

Thompson et al., "Engineering and Identifying Supercharged Proteins for Macromolecule Delivery into Mammalian Cells," Methods in Enzymology, 2012, 503:293-319.

Topf et al., "Regional 'pro-drug' gene therapy: intravenous administration of an adenoviral vector expressing the E. coli cytosine deaminase gene and systemic administration of 5-fluorocytosine suppresses growth of hepatic metastasis of colon carcinoma," Gene Ther., Apr. 1998, 5:507-513.

Townsend et al., "High-frequency modification of plant genes using engineered zinc-finger nucleases," Nature: International Weekly Journal of Science, Nature Publishing Group, May 21, 2009, pp. 442-445.

Tratschin et al., "A human parvovirus, adeno-associated virus, as a eucaryotic vector: transient expression and encapsidation of the procaryotic gene for chloramphenicol acetyltransferase," Mol. Cell. Biol., Oct. 1984, 4:2072-81.

Tratschin et al., "Adeno-Associated Virus Vector for High-Frequency Integration, Expression, and Rescue of Genes in Mammalian Cells," Mol. Cell. Biol., Nov. 1985, 5:3251-60.

Uhlman, "An alternative approach in gene synthesis: use of long selpriming oligodeoxynucleotides for the construction of double-stranded DNA," Gene, Nov. 15, 1988, 71(15): 29-40.

Uhlmann et al., "Distinct methylation profiles of glioma subtypes," Int. J. Cancer, Aug. 2003, 106:52-9.

Urnov et al., "Highly efficient endogenous human gene correction using designed zinc-finger nucleases," Nature, Jun. 2, 2005;435(7042):646-51.

U.S. Final Office Action in U.S. Appl. No. 13/838,520, dated Jul. 15, 2015, 35 pages.

U.S. Non-Final Office Action in U.S. Appl. No. 13/838,520, dated Oct. 6, 2014, 38 pages.

U.S. Non-Final Office Action in U.S. Appl. No. 14/232,067, dated Nov. 17, 2015, 10 pages.

(56) References Cited

OTHER PUBLICATIONS

Van den Brulle et al., "A novel solid phase technology for high-throughput gene synthesis," BioTechniques, 45(3):340-343 (2008).
Vogelstein and Kinzler, "Cancer genes and the pathways they control," Nat. Med., Aug. 2004, 10:789-799.
Voytas and Joung, "Plant Science. DNA binding made easy," Science, Dec. 11, 2009, 326: 1491-1492.
Wagner et al., "Efficient and persistent gene transfer of AAV-CFTR in maxillary sinus," Lancet, Jun. 1998, 351:1702-1703.
Wang et al., "Human PADA4 regulates histone arginine methylation levels via demethylimination," Science, Oct. 8, 2004, 306(5694): 279-283.
Wang et al., "pH-sensitive immunoliposomes mediate target-cell-specific delivery and controlled expression of a foreign gene in mouse," PNAS, Nov. 1987, 84:7851-7855.
Weising et al., "Foreign Genes in Plants: Transfer, Structure, Expression, and Applications," Ann. Rev. Genet., 1988, 22:421-477.
Welsh et al., "Adenovirus-mediated gene transfer for cystic fibrosis: Part A. Safety of dose and repeat administration in the nasal epithelium. Part B. Clinical efficacy in the maxillary sinus," Hum. Gene Ther., Feb. 1995, 6(2):205-218.
Widschwendter and Jones, "DNA methylation and breast carcinogenesis," Oncogene, Aug. 2002, 21:5462-82.
Xu et al., "Cytosine methylation targetted to pre-determined sequences," Nat Genet., Dec. 1997;17(4):376-8.
Yang et al., "Os8N3 is a host disease-susceptibility gene for bacterial blight of rice," Proc Natl Acad Sci USA, Jul. 5, 2006;103(27):10503-8.
Yeager, "Genome Editing in a FLASH ," BioTechniques, Apr. 4, 2012, 2 pages, http://www.biotechniques.com/news/Genome-Editing-in-a-FLASH/biotechniques-329367.html.
Zhang et al., "Programmable Sequence-Specific Transcriptional Regulation of mammilian Genome.Using Designer TAL Effectors," Nature Biotechnology, Feb. 2011, 29(2): 149-153.
Zheng S et al., "Correlations of partial and extensive methylation at the P14ARF locus with reduced MRNA expression in colorectal cancer cell lines and clinicopathological features in primary tumors," Carcinogenesis, Nov. 1, 2000, 21(11): 2057-2064.
Anders and Huber, "Differential expression analysis for sequence count data," Genome Biol., 11(10):R106, Epub Oct. 27, 2010.
Arimondo et al., "Exploring the Cellular Activity of Camptothecin—Triple—Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Bae et al., "Human zinc fingers as building blocks in the construction of artificial transcription factors," Nat Biotechnol., 21(3):275-280, Epub Feb. 18, 2003.
Beerli and Barbas, "Engineering polydactyl zinc-finger transcription factors," Nat Biotechnol., 20(2):135-141, Feb. 2002.
Berg, "Proposed structure for the zinc-binding domains from transcription factor IIIA and related proteins," Proc Natl Acad Sci U S A., 85(1):99-102, Jan. 1988.
Bernstein et al., "Mapping and analysis of chromatin state dynamics in nine human cell types," Nature, 473(7345):43-49, Epub Mar. 23, 2011.
Biancotto et al., "Histone modification therapy of cancer," Adv Genet., 70:341-386, 2010.
Blancafort et al., "Designing transcription factor architectures for drug discovery," Mol Pharmacol., 66(6):1361-1371, Epub Aug. 31, 2004.
Boch et al., "Breaking the code of DNA binding specificity of TAL-type III effectors," Science, 326(5959):1509-1512, Dec. 11, 2009.
Boch et al., "Xanthomonas AvrBs3 family-type III effectors: discovery and function," Annu Rev Phytopathol., 48:419-436, 2010.
Boch, "TALEs of genome targeting," Nat Biotechnol., 29(2):135-136, Feb. 2011.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Boyle et al., "High-resolution mapping and characterization of open chromatin across the genome," Cell., 132(2):311-322, Jan. 25, 2008.
Bulger and Groudine, "Functional and mechanistic diversity of distal transcription enhancers," Cell., 144(3):327-339, Feb. 4, 2011.
Bultmann et al., "Targeted transcriptional activation of silent oct4 pluripotency gene by combining designer TALEs and inhibition of epigenetic modifiers," Nucleic Acids Res., 40(12):5368-77. Epub Mar. 2, 2012.
Cabo and Wysocka, "Modification of enhancer chromatin: what, how, and why?" Mol Cell., 49(5):825-837, Mar. 7, 2013.
Carey et al., "A mechanism for synergistic activation of a mammalian gene by GAL4 derivatives," Nature, 345(6273):361-364, May 24, 1990.
Carroll et al., "Design, construction and in vitro testing of zinc finger nucleases," Nat Protoc., 1(3):1329-1341, 2006.
Carroll, "Progress and prospects: zinc-finger nucleases as gene therapy agents," Gene Ther., 15(22):1463-1468, Epub Sep. 11, 2008.
Cathomen and Joung, "Zinc-finger nucleases: the next generation emerges," Mol Ther., 16(7):1200-1207, Epub Jun. 10, 2008.
Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.Hhal Fused to Zinc Fingers," PLoS ONE, 7(9):E44852 pp. 1-11 (2012).
Chase et al., "Histone methylation at H3K9: evidence for a restrictive epigenome in schizophrenia," Schizophr Res., 149(1-3):15-20, Epub Jun. 28, 2013.
Chen et al., "Crystal structure of human histone lysine-specific demethylase 1 (LSD1)," Proc Natl Acad Sci U S A., 103(38):13956-13961, Epub Sep. 6, 2006.
Chen et al., "Fusion protein linkers: property, design and functionality," Adv Drug Deliv Rev., 65(10):1357-1369, [author manuscript] Epub Sep. 29, 2012.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Chylinski et al., "The tracrRNA and Cas9 families of type II CRISPR-Cas immunity systems," RNA Biol., 10(5):726-737, Epub Apr. 5, 2013.
Cong et al., "Comprehensive interrogation of natural TALE DNA-binding modules and transcriptional repressor domains," Nat Commun., 3:968, [author manuscript] Jul. 24, 2012.
Cong et al., "Multiplex genome engineering using CRISPR/Cas systems," Science, 339(6121):819- 823, Epub Jan. 3, 2013.
Copeland et al., "Targeting genetic alterations in protein methyltransferases for personalized cancer therapeutics," Oncogene., 32(8):939-946, Epub Nov. 19, 2012.
Creyghton et al., "Histone H3K27ac separates active from poised enhancers and predicts developmental state," Proc Natl Acad Sci U S A., 107(50):21931-21936, Epub Nov. 24, 2010.
d'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
Dhami et al., "Genomic approaches uncover increasing complexities in the regulatory landscape at the human SCL (TAL1) locus," PLoS One, 5(2):e9059, Feb. 5, 2010.
Doyle et al., "TAL Effector-Nucleotide Targeter (TALE-NT) 2.0: tools for TAL effector design and target prediction," Nucleic Acids Res., 40(Web Server issue):W117-W122, Epub Jun. 12, 2012.

(56) References Cited

OTHER PUBLICATIONS

Doyle, Computational and experimental analysis of TAL effector-DNA binding [dissertation], Jan. 2013, Iowa State University, Ames, Iowa, 162 pages.

Dreidax et al., "Low p14ARF expression in neuroblastoma cells is associated with repressed histone mark status, and enforced expression induces growth arrest and apoptosis," Hum Mol Genet., 22(9):1735-1745, May 1, 2013.

Eisenschmidt et al., "Developing a programmed restriction endonuclease for highly specific DNA cleavage," Nucleic Acids Res., 33(22):7039-47 (2005).

Elliot and O'Hare, "Intercellular trafficking and protein delivery by a herpesvirus structural protein," Cell, 88(2):223-233, Jan. 24, 1997.

Elrod-Erickson et al., "High-resolution structures of variant Zif268-DNA complexes: implications for understanding zinc finger-DNA recognition," Structure, 6(4):451-464, Apr. 15, 1998.

ENCODE Project Consortium. "An integrated encyclopedia of DNA elements in the human genome," Nature, 489(7414), 57-74, 2012.

Fahraeus et al., "Inhibition of pRb phosphorylation and cell-cycle progression by a 20-residue peptide derived from p16CDKN2/INK4A," Curr Biol., 6(1):84-91, Jan. 1, 1996.

Fonfara et al., "Creating highly specific nucleases by fusion of active restriction endonucleases and catalytically inactive homing endonucleases," Nucleic Acids Res., 40(2):847-860, Epub Sep. 29, 2011.

Garcia-Bustos et al., "Nuclear protein localization," Biochim Biophys Acta., 1071(1):83-101, Mar. 7, 1991.

Garg et al., "Engineering synthetic TAL effectors with orthogonal target sites," Nucleic Acids Res., 40(15):7584-7595, Epub May 11, 2012.

Geißler et al., "Transcriptional Activators of Human Genes with Programmable DNA-Specificity ," PLoS One, 6:e19509 (2011).

GenBank Accession No. NM_001009999.2, "*Homo sapiens* lysine (K)-specific demethylase 1A (KDM1A), transcript variant 1, mRNA," Apr. 6, 2014, 6 pages.

GenBank Accession No. NP_055828.2, "lysine-specific histone demethylase 1A isoform b [*Homo sapiens*]," Apr. 6, 2014, 4 pages.

GenBank Accession No. NM_015013.3, "*Homo sapiens* lysine (K)-specific demethylase 1A (KDM1A), transcript variant 2, mRNA," Apr. 6, 2014, 6 pages.

Gillies et al., "A tissue-specific transcription enhancer element is located in the major intron of a rearranged immunoglobulin heavy chain gene," Cell, 33(3):717-728, Jul. 1983.

Gossen and Bujard, "Tight control of gene expression in mammalian cells by tetracycline-responsive promoters," Proc Natl Acad Sci U S A., 89(12):5547-5551, Jun. 15, 1992.

Grizot et al., "Generation of redesigned homing endonucleases comprising DNA-binding domains derived from two different scaffolds," Nucleic Acids Res., 38(6):2006-2018, Epub Dec. 21, 2009.

Gruen et al., "An in vivo selection system for homing endonuclease activity," Nucleic Acids Res., 30(7):e29, Apr. 1, 2002.

Guo et el., "Hydroxylation of 5-Methylcytosine by TET1 Promotes Active DNA Demethylation in the Adult Brain ," Cell, 145:423-434 (2011).

Harikrishna et al., "Construction and function of fusion enzymes of the human cytochrome P450scc system," DNA Cell Biol., 12(5):371-379, Jun. 1993.

Harrison, "A structural taxonomy of DNA-binding domains," Nature, 353(6346): 715-719, Oct. 24, 1991.

He et al., "Tet-Mediated Formation of 5-Carboxylcytosine and Its Excision by TDG in Mammalian DNA," Science, 333:1303-1307 (2011).

Heintzman et al., "Histone modifications at human enhancers reflect global cell-type-specific gene expression," Nature, 459(7243):108-112, Epub Mar. 18, 2009.

Hockemeye et al., "Genetic engineering of human pluripotent cells using TALE nucleases," Nat. Biotechnol., 29:731-734 (2011).

Hoivik et al., "DNA methylation of intronic enhancers directs tissue-specific expression of steroidogenic factor 1/adrenal 4 binding protein (SF-1/Ad4BP)," Endocrinology, 152(5):2100-2112, Epub Feb. 22, 2011.

Hsu and Zhang, "Dissecting neural function using targeted genome engineering technologies," ACS Chem Neurosci., 3(8):603-610, Epub Jul. 19, 2012.

Huang et al., "Heritable gene targeting in zebrafish using customized TALENs," Nat. Biotechnol., 29:699-700 (2011).

Inaba et al., "Generation of large numbers of dendritic cells from mouse bone marrow cultures supplemented with granulocyte/macrophage colony-stimulating factor," J Exp Med., 176(6):1693-1702, Dec. 1, 1992.

Isalan et al., "A rapid, generally applicable method to engineer zinc fingers illustrated by targeting the HIV-1 promoter," Nat. Biotechnol., 19(7):656-660, Jul. 2001.

Ito et al., "Tet proteins can convert 5-methylcytosine to 5-formylcytosine and 5-carboxylcytosine," Science, 333(6047):1300-1303, Sep. 2, 2011.

Iyer et al., "Prediction of novel families of enzymes involved in oxidative and other complex modifications of bases in nucleic acids," Cell Cycle, 8(11):1698-1710 (2009).

Jamieson et al., "In vitro selection of zinc fingers with altered DNA-binding specificity," Biochemistry, 33(19):5689-5695, May 17, 1994.

Jinek et al., "A programmable dual-RNA-guided DNA endonuclease in adaptive bacterial immunity," Science, 337(6096):816-821, Epub Jun. 28, 2012.

Joung and Sander, "TALENs: a widely applicable technology for targeted genome editing," Nat Rev Mol Cell Biol., 14(1):49-55, Epub Nov. 21, 2012.

Juillerat et al., "Comprehensive analysis of the specificity of transcription activator-like effector nucleases," Nucleic Acids Res., 42(8):5390-5402, Epub Feb. 24, 2014.

Jumlongras et al., "An evolutionarily conserved enhancer regulates Bmp4 expression in developing incisor and limb bud," PLoS One, 7(6):e38568, Epub Jun. 12, 2012.

Karmirantzou and Harnodrakas, "A Web-based classification system of DNA-binding protein families," Protein Eng. 14(7):465-472, Jul. 2001.

Kim et al., "Targeted genome editing in human cells with zinc finger nucleases constructed via modular assembly," Genome Res., 19(7):1279-1288, Epub May 21, 2009.

Kim et al., "Genome editing with modularly assembled zinc-finger nucleases," Nat. Methods, 7(2):91-92, Feb. 2010.

Klug, "Co-chairman's remarks: protein designs for the specific recognition of DNA," Gene, 135(1-2):83-92, Dec. 15, 1993.

Ku et al., "Genomewide analysis of PRC1 and PRC2 occupancy identifies two classes of bivalent domains," PLoS Genet., 4(10):e1000242, Epub Oct. 31, 2008.

Kumar et al., "DNA-Prot: identification of DNA binding proteins from protein sequence information using random forest," J Biomol Struct Dyn., 26(6):679-686, Jun. 2009.

Kumar et al., "Identification of DNA-binding proteins using support vector machines and evolutionary profiles," BMC Bioinformatics, 8:463, Nov. 27, 2007.

Kummerfeld and Teichmann, "DBD: a transcription factor prediction database," Nucleic Acids Res., 34 (Database issue): D74-D81, Jan. 1, 2006.

Lee et al., "An essential role for CoREST in nucleosomal histone 3 lysine 4 demethylation," Nature, 437(7057):432-435, Epub Aug. 3, 2005.

Lee et al., "Three-dimensional solution structure of a single zinc finger DNA-binding domain," Science., 245(4918):635-637, Aug. 11, 1989.

Li et al., "Modularly assembled designer TAL effector nucleases for targeted gene knockout and gene replacement in eukaryotes," Nucleic Acids Res., 39(14):6315-6325, Epub Mar. 31, 2011.

Li et al., "Protein trans-splicing as a means for viral vector-mediated in vivo gene therapy," Hum Gene Ther., 19(9):958-964, Sep. 2008.

Li et al., "Transcription activator-like effector hybrids for conditional control and rewiring of chromosomal transgene expression," Sci Rep., 2:897, Epub Nov. 28, 2012.

(56) References Cited

OTHER PUBLICATIONS

Li et al., "TAL nucleases (TALNs): hybrid proteins composed of TAL effectors and FokI DNA-cleavage domain," Nucl Acids Res, 39:359-372 (2011).
Lin et al., "iDNA-Prot: identification of DNA binding proteins using random forest with grey model," PLoS One., 6(9):e24756, Epub Sep. 15, 2011.
Lippow et al., "Creation of a type IIS restriction endonuclease with a long recognition sequence," Nucleic Acids Res., 37(9):3061-3073, May 2009.
Liu et al., "Regulation of an endogenous locus using a panel of designed zinc finger proteins targeted to accessible chromatin regions. Activation of vascular endothelial growth factor A," J Biol Chem., 276(14):11323-11334, Epub Jan. 5, 2001.
Liu et al., "Validated zinc finger protein designs for all 16 GNN DNA triplet targets," J. Biol. Chem., 277(6):3850-3856, Epub Nov. 28, 2001.
Mabaera et al., "Developmental- and differentiation-specific patterns of human γ- and β-globin promoter DNA methylation," Blood, 110(4):1343-52 (2007).
Madrigal and Krajewski, "Current bioinformatic approaches to identify DNase I hypersensitive sites and genomic footprints from DNase-seq data," Front Genet., 3:230, eCollection 2012, Oct. 31, 2012.
Maeder et al., "Rapid "open-source" engineering of customized zinc-finger nucleases for highly efficient gene modification," Mol Cell., 31(2):294-301, Jul. 25, 2008.
Maeder et al., "Robust, synergistic regulation of human gene expression using TALE activators," Nat Methods., 10(3):243-245, Epub Feb. 10, 2013.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Mahfouz et al., "Targeted transcriptional repression using a chimeric TALE-SRDX repressor protein," Plant Mol Biol., 78(3):311-321, Epub Dec. 14, 2011.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock In and Sequence Modulation Mediated by a Psoralen-linked Triplex-forming Oligonucleotide," J Biol Chem., 283(17):11244-52 (2008).
Mandell and Barbas et al., "Zinc Finger Tools: custom DNA-binding domains for transcription factors and nucleases," Nucleic Acids Res., 34(Web Server issue):W516-W523, Jul. 1, 2006.
Maurano et al., "Systematic localization of common disease-associated variation in regulatory DNA," Science, 337(6099):1190-1195, Epub Sep. 5, 2012.
McDaniell et al., "Heritable individual-specific and allele-specific chromatin signatures in humans," Science, 328(5975):235-239, [author manuscript] Epub Mar. 18, 2010.
Mendenhall et al., "Locus-specific editing of histone modifications at endogenous enhancers," Nat Biotechnol., 31(12):1133-1136, Epub Sep. 8, 2013.
Metzger et al., "LSD1 demethylates repressive histone marks to promote androgen-receptor-dependent transcription," Nature, 437(7057):436-439, 2005.
Miller et al., "A TALE nuclease architecture for efficient genome editing," Nat. Biotechnol., 29(2):143-148, Epub Dec. 22, 2010.
Miller et al., "Repetitive zinc-binding domains in the protein transcription factor IIIA from Xenopus oocytes," EMBO J., 4(6):1609-1614, Jun. 1985.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Morbitzer et al., "Assembly of custom TALE-type DNA binding domains by modular cloning," Nucl Acids Res., 39:5790-5799 (2011).
Moscou and Bogdanove, "A simple cipher governs DNA recognition by TAL effectors," Science, 326(5959):1501, Dec. 11, 2009.
Mussolino and Cathomen, "TALE nucleases: tailored genome engineering made easy," Curr Opin Biotechnol., 23(5):644-650, Epub Feb. 17, 2012.
Neering et al., "Transduction of primitive human hematopoietic cells with recombinant adenovirus vectors," Blood, 88(4):1147-1155, Aug. 15, 1996.
Ng et al., "In vivo epigenomic profiling of germ cells reveals germ cell molecular signatures," Dev Cell., 24(3):324-333, Epub Jan. 24, 2013.
Noonan and McCallion, "Genomics of long-range regulatory elements," Annu Rev Genomics Hum Genet., 11:1-23, 2010.
Oligino et al., "Drug inducible transgene expression in brain using a herpes simplex virus vector," Gene Ther., 5(4):491-496, Apr. 1998.
Ong and Corees, "Enhancer function: new insights into the regulation of tissue-specific gene expression," Nat Rev Genet., 12(4):283-293, Epub Mar. 1, 2011.
Palva et al., "Secretion of interferon by Bacillus subtilis," Gene, 22(2-3):229-235, May-Jun. 1983.
Pavletich and Pabo, "Zinc finger-DNA recognition: crystal structure of a Zif268-DNA complex at 2.1 A," Science, 252(5007):809-817, May 10, 1991.
Perez-Pinera et al., "Synergistic and tunable human gene activation by combinations of synthetic transcription factors," Nat Methods., 10(3):239-342, Epub Feb. 3, 2013.
Pingoud and Silva, "Precision genome surgery," Nat Biotechnol., 25(7):743-744, Jul. 2007.
Qi et al., "Repurposing CRISPR as an RNA-guided platform for sequence-specific control of gene expression," Cell, 152(5):1173-1183, Feb. 28, 2013.
Rada-Iglesias et al., "A unique chromatin signature uncovers early developmental enhancers in humans," Nature, 470(7333):279-283, Epub Dec. 15, 2010.
Ram et al., "Combinatorial patterning of chromatin regulators uncovered by genome-wide location analysis in human cells," Cell, 147(7):1628-1639, Dec. 23, 2011.
Ramirez et al., "Unexpected failure rates for modular assembly of engineered zinc fingers," Nat Methods., 5(5):374-375, May 2008.
Rebar and Pabo, "Zinc finger phage: affinity selection of fingers with new DNA-binding specificities," Science, 263(5147):671-673, Feb. 4, 1994.
Rendahl et al., "Regulation of gene expression in vivo following transduction by two separate rAAV vectors," Nat. Biotechnol., 16(8):757-761, Aug. 1998.
Reyon et al., "Engineering designer transcription activator-like effector nucleases (TALENs) by REAL or REAL-Fast assembly" Curr Protoc Mol Biol., Chapter 12:Unit 12.15, [author manuscript] Oct. 2012.
Reyon et al., "FLASH assembly of TALENs for high-throughput genome editing," Nat Biotechnol., 30(5):460-465, May 2012.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:2301 12 pages (2010).
Rosenbloom et al., "ENCODE whole-genome data in the UCSC Genome Browser: update 2012," Nucleic Acids Res., 40(Database issue):D912-D917, Epub Nov. 9, 2011.
Rothman, "Mechanisms of intracellular protein transport," Nature, 372(6501):55-63, Nov. 3, 1994.
Sabo et al, "Genome-scale mapping of DNase I sensitivity in vivo using tiling DNA microarrays," Nat Methods., 3(7):511-518, Jul. 2006.

(56) References Cited

OTHER PUBLICATIONS

Sabo et al., "Discovery of functional noncoding elements by digital analysis of chromatin structure," Proc Natl Acad Sci U S A., 101(48):16837-16842, Epub Nov. 18, 2004.
Sander et al., "Targeted gene disruption in somatic zebrafish cells using engineered TALENs," Nat. Biotechnol., 29:697-698 (2011).
Sanjana et al., "A transcription activator-like effector toolbox for genome engineering," Nat Protoc., 7(1):171-192, Jan. 5, 2012.
Schleifman et al., "Triplex-mediated gene modification," Methods Mol. Biol., 435:175-190, 2008.
Scholze & Boch, "TAL effectors are remote controls for gene activation," J. Curr. Opin. Microbiol, 14:47-53 (2011).
Segal et al., "Evaluation of a modular strategy for the construction of novel polydactyl zinc finger DNA-binding proteins," Biochemistry, 42(7):2137-2148, Feb. 25, 2003.
Shi et al., "Histone demethylation mediated by the nuclear amine oxidase homolog LSD1," Cell, 119(7):941-953, Dec. 29, 2004.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Sipione et al., "Insulin expressing cells from differentiated embryonic stem cells are not beta cells," Diabetologia, 47(3):499-508. Epub Feb. 14, 2004.
Stadler et al., "DNA-binding factors shape the mouse methylome at distal regulatory regions," Nature, 480(7378):490-495, Dec. 14, 2011.
Stoddard, "Homing endonuclease structure and function," Q. Rev. Biophys., 38(1): 49-95, Epub Dec. 9, 2005.
Stott et al., "The alternative product from the human CDKN2A locus, p14(ARF), participates in a regulatory feedback loop with p53 and MDM2," EMBO J., 17(17):5001-5014, Sep. 1, 1998.
Streubel et al., "TAL effector RVD specificities and efficiencies," Nat Biotechnol., 30(7):593-595, Jul. 10, 2012.
Tahiliani et al., "Conversion of 5-Methylcytosine to 5-Hydroxymethylcytosine in Mammalian DNA by MLL Partner TET1," Science, 324:930-935 (2009).
Tan et al., "Zinc-finger protein-targeted gene regulation: genomewide single-gene specificity," Proc Natl Acad Sci U S A., 100(21):11997-2002, Epub Sep. 26, 2003.
Tesson et al., "Knockout rats generated by embryo microinjection of TALENs," Nat. Biotechnol., 29:695-696 (2011).
Thurman et al., "The accessible chromatin landscape of the human genome," Nature, 489(7414):75-82, Sep. 6, 2012.
Tjong and Zhou, "DISPLAR: an accurate method for predicting DNA-binding sites on protein surfaces," Nucleic Acids Res., 35(5):1465-1477, Epub Feb. 6, 2007.
Tremblay et al., "Transcription activator-like effector proteins induce the expression of the frataxin gene," Hum Gene Ther., 23(8):883-890, Epub Jul. 20, 2012.
Valton et al., "Overcoming transcription activator-like effector (TALE) DNA binding domain sensitivity to cytosine methylation," J Biol Chem., 287(46):38427-38432, Epub Sep. 26, 2012.
Visel et al., "Genomic views of distant-acting enhancers," Nature, 461(7261):199-205, Sep. 10, 2009.
Wang et al., "An integrated chip for the high-throughput synthesis of transcription activator-like effectors," Angew Chem Int Ed Engl., 51(34):8505-8508, Epub Jul. 23, 2012.
Wang et al., "Positive and negative regulation of gene expression in eukaryotic cells with an inducible transcriptional regulator," Gene Ther., 4(5):432-441, May 1997.
Weber et al., "Assembly of Designer TAL Effectors by Golden Gate Cloning," PLoS ONE, 6:e19722 (2011).
Whyte et al., "Enhancer decommissioning by LSD1 during embryonic stem cell differentiation," Nature, 482(7384):221-225, Feb. 1, 2012.

Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 1(3):1637-1652, 2006.
Wu et al., "Building zinc fingers by selection: toward a therapeutic application," Proc Natl Acad Sci U S A., 92(2):344-348, Jan. 17, 1995.
Wu et al., "Custom-designed zinc finger nucleases: what is next?" Cell Mol Life Sci., 64(22):2933-2944, Nov. 2007.
Wu, "The 5' ends of *Drosophila* heat shock genes in chromatin are hypersensitive to DNase I," Nature, 286(5776):854-860, Aug. 28, 1980.
Xie et al., "DNA hypomethylation within specific transposable element families associates with tissue-specific enhancer landscape," Nat Genet., 45(7):836-841, Epub May 26, 2013.
Xu et al., "Pioneer factor interactions and unmethylated CpG dinucleotides mark silent tissue-specific enhancers in embryonic stem cells," Proc Natl Acad Sci U S A., 104(30):12377-12382, Epub Jul. 18, 2007.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yoon and Brem, "Noncanonical transcript forms in yeast and their regulation during environmental stress," RNA, 16(6):1256-1267, Epub Apr. 26, 2010.
Yost et al., "Targets in epigenetics: inhibiting the methyl writers of the histone code," Curr Chem Genomics, 5(Suppl 1):72-84, Epub Aug. 22, 2011.
Zhang et al., "Efficient construction of sequence-specific TAL effectors for modulating mammalian transcription," Nat Biotechnol., 29(2):149-153, Epub Jan. 19, 2011.
Zhang et al., "Genome-wide identification of regulatory DNA elements and protein-binding footprints using signatures of open chromatin in *Arabidopsis*," Plant Cell., 24(7):2719-2731. Epub Jul. 5, 2012.
Zhang et al., "Supplementary Information, Data S1, TET1 is a 5mC hydroxylase in vitro" from, "TET1 is a DNA-binding protein that modulates DNA methylation and gene transcription via hydroxylation of 5-methylcytosine," Cell Res., 6 pages, 2010.
Zhang et al., "Transcription activator-like effector nucleases enable efficient plant genome engineering," Plant Physiol., 161(1):20-27, Epub Nov. 2, 2012.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zitzewitz et al., "Probing the folding mechanism of a leucine zipper peptide by stopped-flA4:A48ism spectroscopy," Biochemistry, 34(39):12812-12819, Oct. 3, 1995.
International Search Report and Written Opinion for PCT/US2014/015343, dated Jun. 3, 2014, 17 pages.
International Preliminary Report on Patentability for PCT/US2014/015343, dated Aug. 20, 2015, 7 pages.
U.S. Appl. No. 13/838,520, filed Mar. 15, 2013.
U.S. Appl. No. 14/435,065, filed Apr. 10, 2015.
Paques et al., "Meganucleases and DNA double-strand break-induced recombination: persectives for gene thereapy," Current Gene Therapy, Bentham Science Publishers Ltd, Feb. 1, 2007, 7(1): 49-66.
Medenhall et al., "Identification of promoter targets of enhancers by epigenetic knockdown using TAL DNA binding proteins," Epigenetics & Chromatin, 2013, 6(Suppl): 1-2.
Office Action in European Application No. 12814750.1, dated Mar. 8, 2017, 7 pages.
Office Action in Japanese Appliaction No. 2014-520317, dated Jan. 17, 2017, 6 pages (with English translation).
Office Action in U.S. Appl. No. 13/838,520, dated Feb. 24, 2017, 49 pages.

(56) References Cited

OTHER PUBLICATIONS

Office Action in U.S. Appl. No. 14/435,065, dated Jan. 26, 2017, 22 pages.
European Office Action in European Application No. 13797024.0, dated Jul. 18, 2017, 9 pages.
Frasier et al., "Different Binding Properties and Function of CXXC Zinc Finger Domains in Dnmt1 and Tet1," PLOS One, Feb. 2011, 6: e16627.
Li et al. Regulatory mechanisms of tumor suppressor p16AINK4A and their relevance to cancer. Biochemistry, vol. 50, pp. 5566-5582, May 27, 2011.
Office Action in U.S. Appl. No. 14/435,065, dated Jul. 27, 2017, 25 pages.
Pekowska et al. H3K4 tri-methylation provides an epigenetic signature of active enhancers. The EMBO Journal, vol. 30, pp. 4198-4210, Aug. 16, 2011, including supplementary figures S1-S11, printed as pp. 1/13-13/13.
Extended European Search Report in Application No. 17205413.2, dated Mar. 23, 2018, 7 pages.
Jia et al., "Cancer gene therapy targeting cellular apoptosis machinery," Cancer Treatment Reviews, 2012, 38:868-879.
Maeder et al, "Upregulation of the Pluripotency-Associated miRNA 302-367 Cluster 1 Using Engineered Transcription Activator-Like Effector(TALE) Activators," Molecular Therapy, 2012, 20:S193 499.
Office Action in European Application No. 13797024.0, dated Mar. 16, 2018, 8 pages.
Office Action in European Application No. 13845212.3, dated Feb. 15, 2018, 4 pages.
Office Action in Japanese Application No. 2015-557129, dated Dec. 19, 2017, 8 pages (with English translation).
Tani et al., "Updates on current advances in gene therapy," The West Indian Medical Journal, 2011, 60:188-194.
Verma and Weitzman, "Gene Therapy: Twenty-first century medicine," Annual Review of Biochemistry, 2005, 74:711-738.
Yan and Higgins, "Drugging the undruggable: Transcription therapy for cancer," Biochinnica et Biophysica Acta, 2013, 1835:76-85.
Beerli et al., "Toward controlling gene expression at will: Specific regulation of the erbB-2/HER-2 promoter using polydactyl zinc finger proteins constructed from modular building blocks," Prox. Nat'l. Acad. Sci. U.S.A., Dec. 1998, 95:14628-14633.
GenBank Accession No. FJ176909.1, "*Xanthomonas oryzae* pv. oryzae clone 041 avirulence/virulence factor repeat domain protein-like gene, complete sequence," dated Sep. 30, 2008 [retrieved on Aug. 30, 2018]. Retrieved from the Internet: URL <https://www.ncbi.nlm.nih.gov/nuccore/FJ176909.1/> 2 pages.
GEO Sample G5M1008573, Duke DnaseSeq HEK293T, Sep. 25, 2012, printed as pp. 1/2-282 from https://www.ncbi.nlin.nih.gov/geo/query/acc.cgi?acc=GSM1008573. 2 pages
Greer et al., "Histone methylation: a dynamic mark in health, disease and inheritance," Nature Reviews Genetics, vol. 13, pp. 343-357, published online Apr. 3, 2012.
Kamijo et al., "Tumor spectrum in ARD-deficient mice," Cancer Research, May 1999, 59:2217-2222.
Office Action in Australian Application No. 2017204819, dated Sep. 7, 2018, 7 pages.
Office Action in Canadian Application No. 2,841,710, dated May 11, 2018, 4 pages.
Office Action in Japanese Application No. 2017-136828, dated Sep. 11, 2018, 7 pages (with English translation).
Extended European Search Report in Application No. 18191841.8, dated May 24, 2019, 9 pages.
Extended European Search Report in Application No. 18214166.3, dated Feb. 4, 2019, 9 pages.
Office Action in Australian Application No. 2014214719, dated Feb. 14, 2019, 3 pages.
Office Action in Canadian Application No. 2,841,710, dated Apr. 15, 2019, 4 pages.
Office Action in Japanese Application No. 2017-136828, dated Aug. 27, 2019, 7 pages (with English Translation).
Partial European Search Report in Application No. 18191841.8, dated Jan. 30, 2019, 17 pages.
UCSC Genome Browser (Human Feb. 2009 (GRCh37/hg19) Assembly, chr12:2,162,284-2,162,418 with HEK293T DNase 1 HS track from ENCODE/DUKE, printed from https://genome.ucwsc.edu as page 1/1 on Jun. 28, 2019. (Year: 2019).
UCSC Genome Browser (Human Feb. 2009 (GRCh37/hg19) Assembly, chr9:21,440,329-21,440,478 with HEK293T DNase 1 HS track from ENCODE/DUKE, printed from https://genome.ucwsc.edu as page 1/1 on Jun. 25, 2019. (Year: 2019).
CA Office Action in Canadian Appln. No. 2,900,338, dated Dec. 16, 2019, 6 pages.
EP Extended European Search Report in EP Appln. No. 19191923.2, dated Feb. 14, 2020, 6 pages.
JP Office Action in Japanese Application No. 2018-223519, dated Jan. 7, 2020, 7 pages. (with English Translation).

\* cited by examiner excluded content tion of a target gene; thereby making a TALE-activator that increases transcription of the target gene.

In some embodiments, the TALE repeat array is 16.5 to 22.5 repeats (the C-terminal repeat is typically shorter and is referred to as a "half repeat").

In some embodiments, the transactivation domain comprises a VP16, VP64 or NF-KB p65 domain, preferably VP64.

In an additional aspect, the invention provides methods for increasing transcription of a target sequence in a cell, the method comprising contacting the cell with a TALE-activator made by a method described herein.

In an additional aspect, the invention provides methods for increasing transcription of a target sequence in a cell, by contacting the cell with two or more TALE-activators made by a method described herein.

In some embodiments, at least one of the two or more TALE-activators comprises VP64, and at least one of the two or more TALE-activators comprises NF-KB p65 domain.

The subsequences identified by the methods described herein are also referred to as TALE-activator binding sites.

In some embodiments of the methods describe herein wherein the first (5') nucleotide in the subsequence is a thymine, the subsequence includes the DNA bases (e.g., 17-23 bases) that are each specified by a single canonical TALE-repeat domain, and an additional T base that is located just 5' to the first base contacted by the amino-terminal-most canonical TALE-repeat domain; this T base is part of the subsequence (i.e., the subsequence includes the 5' T), but in preferred embodiments is not bound by one of the canonical TALE repeat domains (the 5' T is believed to contact the N terminus of the TALE that precedes the first canonical TALE-repeat domains; there is a pseudo-repeat-like domain there that is believed to make the contact to this T). See, e.g., Joung and Sander, Nature Reviews Molecular Cell Biology 14, 49-55 (2013). In some embodiments where the 5' nucleotide is other than thymine, the subsequence can be 17-23 nucleotides long, and in some embodiments is 17-18 nucleotides long, and therefore consists entirely of nucleotides that contact the TALE repeat domains.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
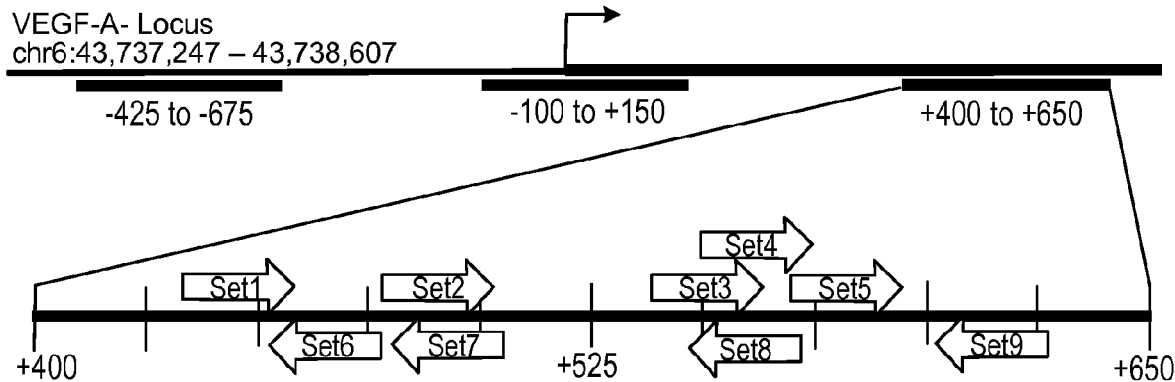
FIGS. 1A-B Activities of 54 variable length TALE-activators targeted to the endogenous human VEGF-A gene. (a) Schematic depicting the human VEGF-A promoter region. The transcription startpoint is indicated with a black arrow and previously published DNase I hypersensitive regions[19] are shown as grey bars. The DNase I hypersensitive region located between positions +400 to +650 relative to the transcription start site has been expanded, with red arrows indicating the locations and orientations of the 26 bp sites bound by the longest length TALE-activator (harboring 24.5 TAL effector repeats) in each set. (b) Activation of VEGF-A protein expression in 293 cells by 54 variable-length TALE-activators. Fold-activation values were calculated as described in Methods. Each TALE-activator was assayed in triplicate and error bars represent standard errors of the mean. Asterisks indicate fold-activation values that are outliers (assuming a normal distribution) relative to other values in the same set. All activators tested (except the 14.5-repeat activator from set 7) induced fold-activation of VEGF-A expression to a value significantly greater than 1, as determined by a one-sided, paired t-test.

Although TALE-activators have a broad range of potential applications, the low activities and restricted targeting range of these proteins as described in the literature to date raise concerns about the robustness of this technology. Published TALE-activators made for endogenous genes have generally shown very modest activities[3-6, 8, 9]—13 of the 26 previously described proteins (for which quantitative information is available) induced target gene expression by three-fold or more and only 4 out of 26 activated by five-fold or more (Table 1).

TABLE 1

| Gene Targeted | Organism/ Cell line | TALE Length (# of repeats) | Activation Domain | Approximate Fold Activation | Ref. | Archi- techture | Target Site | SEQ ID NO: |
|---|---|---|---|---|---|---|---|---|
| NTF3 | Human HEK293 cells | 17.5 | VP16 | 30 | 1 | A | TGGAGCCATCTGGC CGGGT* | 1. |
| SOX2 | mouse | 12.5 | VP16 | 5.5 | 2 | B | TTTATTCCCTGACA | 2. |
| KLF4 | mouse | 12.5 | VP16 | 2.2 | | | TTCTTACTTATAAC | 3. |
| OCT4 | mouse | 12.5 | VP16 | no activation | | | TTCTCCCACCCCCA | 4. |
| C-MYC | mouse | 12.5 | VP16 | no activation | | | TCCCGAGTCCCCAA | 5. |
| PUMA | Human HEK293T-Rex cells | 17.5 | VP16 | 1.5 | 3 | C | TACTTGGAGGCAGT CAAGT* | 6. |
| IFNa1 | Human HEK293T-Rex cells | 19.5 | VP16 | 3.1 | | | TGGAAAGTGGCCCA GAAGCAT | 7. |
| IFNb1 | Human HEK293T-Rex cells | 17.5 | VP16 | 3.5 | | | TCTCATATAAATAG GCCAT | 8. |
| FXN | Human 293FT cells | 13.5 | VP64 | 0.9 to 1.7 | 4 | B | TCCCTTGGGTCAGG* | 9. |
| | | | | 1.1 to 1.6 | | | TGGTTGCACTCCGT* | 10. |
| | | | | 1.0 to 1.6 | | | TGCTTTGCACAAAG* | 11. |
| | | | | 1.1 to 2.0 | | | TGCACGAATAGTGC* | 12. |
| | | | | 1.1 to 1.4 | | | TAGTGCTAAGCTGG* | 13. |
| | | | | 1.7 to 3.1 | | | TCCTGAGGTCTAAC* | 14. |
| | | | | 1.1 to 1.5 | | | TGAGGTCTAACCTC* | 15. |
| OSGIN2 | Human U-2OS cells | 18.5 | VP64 | 4.8 | 5 | D | TCCTCCCCACCTTT AATTTT* | 16. |
| ZC3H10 | Human U-2OS cells | 18.5 | VP64 | 1.3 | | | TACCATATCCCATC CAACTC | 17. |
| ROCK1 | Human HeLa cells | 16.5 | VP64 | n.d. | 6 | E | TCTCCTCGTCAGAA GTCT | 18. |
| CACNA1C | Human 293FT cells | 16.5 | VP64 | 5.5 | 7 | B | TCGGCCCCTGCCGG CCCA | 19. |
| | | | | 2.75 | | | TCGGCCCCTGCCGG CCCA | 20. |
| | | | | 4.5 | | | TCGGCCCCTGCCGG CCCA | 21. |
| | | | | 6 | | | TCGGCCCCTGCCGG CCCA | 22. |
| | | | | 3 | | | TGGTAGACCTTAGG GCTA | 23. |
| | | | | 1.5 | | | TGGTAGACCTTAGG GCTA | 24. |
| | | | | 4 | | | TGGTAGACCTTAGG GCTA | 25. |
| | | | | 3.5 | | | TGGTAGACCTTAGG GCTA | 26. |

TABLE 1-continued

| Gene Targeted | Organism/ Cell line | TALE Length (# of repeats) | Activation Domain | Approximate Fold Activation | Ref. | Archi- techture | Target Site | SEQ ID NO: |
|---|---|---|---|---|---|---|---|---|
| OCT4 | Mouse ES cells | 17.5 | VP16 | 4 | 8 | F | TCCCACCCCCACAG CTCTG | 27. |
|  | Mouse neural stem cells |  |  | 30** |  |  |  | 28. |
| Bs3 | pepper plants | 13.5 | native AvrHah1 activation domain | n.d. | 9 | G | TGTAAACCTGACCC T | 29. |

*sequence within a DNase1 hypersensitive site
**Activation observed in the presence of VPA and/or 5-azadC
Architecture Key:
A = originally referenced in Miller et al., Nature Biotech 2011
B = originally referenced in Zhang et al., Nature Biotech 2011
C = originally referenced in Geissler et al., PLoS ONE 2011
D = originally described in Garg et al., NAR 2012
E = originally described in Huang et al., Nature Biotech 2011
F = originally described in Morbitzer et al., NAR 2011
G = originally described in Cermak et al., NAR 2011

One potential explanation for these observed low activities is that certain DNA sequences may be suboptimal for targeting by TALE-activators, a concept recently codified by Bogdanove and colleagues in five computationally-derived guidelines for choosing target sites (Doyle, E. L. et al., Nucleic Acids Res 40, W117-122 (2012); discussed further below). Consistent with this, 19 of the 20 target sites for the 26 published TALE-activators described above fail to meet one or more of these five guidelines (Table 2). Another potential cause for the low fold-activation values observed could be that some of the various TALE-activator architectures used in previous studies may not be optimal, as discussed further below. However, the seven different architectures used to date to construct TALE-activators tested on endogenous gene targets[2, 4, 5, 7, 9, 10] have been evaluated on only relatively small numbers of sites, making it difficult to evaluate their individual efficiencies (Tables 1 and 2). Thus, a robust, well-validated TALE-activator platform with a broad targeting range has yet to be identified for investigators interested in using these proteins.

Described herein are TALE-activators constructed on a single common architecture in which parameters that do and do not affect the activities of these proteins in human cells are systematically defined. As shown herein, TALE-activators of certain critical defined lengths can robustly activate transcription of not only protein-coding, but also non-coding microRNA (miRNA), genes in human cells. In addition, TALE-activators made on the present platform are not constrained by four of five previously described computationally-derived guidelines that restrict target site choice (Doyle, E. L. et al., Nucleic Acids Res 40, W117-122 (2012)), thereby greatly expanding the targeting range for these proteins. Finally, levels of target gene expression can be variably tuned by altering the specific activation domain used and/or by exploiting the ability of TALE-activators, like naturally occurring transcription factors, to function synergistically. Taken together, the present data provide clear and large-scale evidence that, contrary to the published literature, TALE-activators are indeed a robust platform for controlling expression of essentially any endogenous gene of interest over a wide dynamic range in human cells.

Guidelines for Choosing Monomeric TALE-activator Binding Sites and Effects on Targeting Range Cermak et al. originally proposed five guidelines for identifying optimal TALE-activator binding sites of engineered dimeric TALENs (Cermak, T. et al. Nucleic Acids Res 39, e82 (2011)). These guidelines were computationally derived from data on the binding preferences of naturally occurring TAL effectors but were not prospectively tested experimentally. As summarized previously (Doyle, E. L. et al. Nucleic Acids Res 40, W117-122 (2012)), the Cermak guidelines can be stated as follows:
1. The nucleotide just 5' to the first nucleotide in the TALE-activator binding site should be a thymine.
2. The first nucleotide of the TALE-activator binding site should not be a thymine.
3. The second nucleotide of the TALE-activator binding site should not be an adenosine.
4. The 3' most nucleotide of the TALE-activator binding site should be a thymine.
5. The base composition of the TALE-activator binding site should not vary from the observed percent composition of naturally occurring binding sites by more than 2 standard deviations. The percent composition of naturally occurring TAL effector repeat array binding sites was determined to be: A=31±16%, C=37±13%, G=9±8%, T=22±10%. Therefore, the base composition of TALE-activator binding sites should be: A=0-63%, C=11-63%, G=0-25%, T=2-42%.

In a previous large-scale study, it was demonstrated that highly active dimeric TALENs can be made for target binding sites that violate one or more of guidelines 2 through 5 (none of the sites targeted violated guideline 1) (Reyon, D. et al. Nat Biotechnol 30, 460-465 (2012)). As demonstrated herein, no significant correlation exists between the number of guideline violations and the activities of the engineered dimeric TALENs (Reyon, D. et al. (2012)). These results strongly suggested that guidelines 2 through 5 do not need to be followed when choosing target sites for dimeric TALENs.

More recently, Doyle et al. suggested that target binding site selection for monomeric TAL effector-based proteins should be limited by these same five guidelines (Doyle, E. L. et al. Nucleic Acids Res 40, W117-122 (2012)). The TALE-NT 2.0 web-based software tool (boglab.plp.iastate.edu) recently developed by Bogdanove and colleagues (Doyle, E. L. et al. Nucleic Acids Res 40, W117-122 (2012)) also applies these five guidelines in its default settings when choosing target sites for monomeric TAL effector repeat arrays used in TALE-activators.

D. The base composition of the TALE-activator binding site varies from the observed percent composition of naturally occurring binding sites by more than 2 standard deviations, i.e., is other than A=0-63%, C=11-63%, G=0-25%, T=2-42%.

In some embodiments, one or more, e.g., all, of B-D are not true.

TABLE 2

| Reference | Gene Targeted | TALE length (# of RVDs) | Binding site | Cermak Guidelines | | | | | Total Guideline Violations | SEQ ID NO: |
|---|---|---|---|---|---|---|---|---|---|---|
| | | | | 1 | 2 | 3 | 4 | 5 | | |
| 2 | NTF3 | 17.5 | CGGAGCCATCTGGCCGGGT | X | | | | X | 2 | 30. |
| 3 | SOX2 | 12.5 | TTTATTCCCTGACA | | X | | X | | 2 | 31. |
| | KLF4 | 12.5 | TTCTTACTTATAAC | | X | | X | X | 3 | 32. |
| | OCT4 | 12.5 | TCCCGAGTCCCCAA | | | | X | | 1 | 33. |
| | C-MYC | 12.5 | TTCTCCCACCCCCA | | X | | X | X | 3 | 34. |
| 4 | PUMA | 17.5 | TACTTGGAGGCAGTCAAGT | | | | X | | 1 | 35. |
| | IFNa1 | 19.5 | TGGAAAGTGGCCCAGAAGCAT | | | | X | | 1 | 36. |
| | IFNb1 | 17.5 | TCTCATATAAATAGGCCAT | | | | | | 0 | 37. |
| 6 | frataxin | 13.5 | CTCCCTTGGGTCAGG | X | | | X | X | 3 | 38. |
| | | | CTGGTTGCACTCCGT | X | | | | X | 2 | 39. |
| | | | GTGCTTTGCACAAAG | X | | | X | | 2 | 40. |
| | | | ATGCACGAATAGTGC | X | | | X | X | 3 | 41. |
| | | | ATAGTGCTAAGCTGG | X | | | X | X | 3 | 42. |
| | | | TTCCTGAGGTCTAAC | | | | X | | 1 | 43. |
| | | | CTGAGGTCTAACCTC | X | | X | X | | 3 | 44. |
| 5 | OSGIN2 | 18.5 | TCCTCCCCACCTTTAATTTT | | | | | X | 1 | 45. |
| | ZC3H10 | 18.5 | TACCATATCCCATCCAACTC | | | | X | | 1 | 46. |
| 7 | ROCK1 | 16.5 | TCTCCTCGTCAGAAGTCT | | | | | | 0 | 47. |
| 8 | CACNA1C | 16.5 | TCGGCCCCTGCCGGCCCA | | | | X | X | 2 | 48. |
| | | | TGGTAGACCTTAGGGCTA | | | | X | X | 2 | 49. |
| 10 | OCT4 | 17.5 | TCCCACCCCCACAGCTCTG | | | | X | | 1 | 50. |
| 18 | Bs3 | 13.5 | TGTAAACCTGACCCT | | | | | | 0 | 51. |

* Exact site targeted is not present in the human genome
** Able to activate only when used in combination with VPA and 5-aza The implementation of these prior art guidelines has the effect of substantially limiting the targeting range of engineered monomeric TALE-activators. For example, application of the five guidelines restricts the identification of a targetable 18 bp site (bound by a 16.5 TAL effector repeat array) to once in every 27 bps of random DNA sequence. By contrast, relaxing guidelines 2 through 5, enables a targetable 18 bp site to be found once in every two bps of random DNA, a more than 13-fold improvement in targeting range.

Thus, in some embodiments, the present methods include selecting a TALE-activator binding site wherein the binding site is within a DNaseI hypersensitive site; wherein the nucleotide just 5' to the first nucleotide in the canonical TALE-repeat domain binding site is a thymine; and wherein the binding site is 18 to 24 bps in length (including the 5' T).

In some embodiments, one or more of the following is also true:
A. The first nucleotide of the TALE-activator binding site is a thymine;
B. The second nucleotide of the TALE-activator binding site is an adenosine;
C. The 3' most nucleotide of the TALE-activator binding site is not a thymine; and/or Methods for Engineering TALE-Activators Described herein is large-scale validation and optimization of a TALE-activator architecture that can be used to robustly activate expression of endogenous genes in human cells. Systematic testing of the effect of TAL effector repeat number on this architecture demonstrated that TALE-activators composed of 16.5 to 22.5 repeats (targeting sites 18 to 24 bps in length, with a T at the 5' end of the binding site) possess optimal activities. The data also provide clear-cut experimental evidence showing that TALE-activators made on this architecture do not need to adhere to four of five published computationally-derived guidelines (Doyle, E. L. et al., Nucleic Acids Res 40, W117-122 (2012)), thereby greatly expanding the targeting range of this platform to one 18 bp site in every two bps of random DNA sequence. These parameters were validated by prospectively making TALE-activators targeted to sites within known or predicted DNase I hypersensitive sites and demonstrating high activities and high success rates on protein-coding and miRNA cluster genes, a result that stands in contrast to previously published studies that described less robust activation (Table 1).

Thus, the methods described herein include selecting a target sequence of interest, preferably a target sequence that is part of or comprises a regulatory region, e.g., a promoter, of a target gene. In some embodiments, the methods include selecting a target sequence that is in a known DNase I hypersensitive region, e.g., based on comparison to one or more databases. In some embodiments, the methods include performing a DNase I hypersensitivity assay as known in the art to identify a target sequence that is within a DNase I hypersensitivity region.

The methods further include identifying potential (or candidate) TALE-activator binding sites based on the guidelines set forth herein, i.e., TALE-activator binding sites 18-24 bp in length preferably including the 5' T. In some embodiments, users can change this length constraint, e.g., by entering a new value in a length input box. The studies described herein suggest that TAL effector repeat arrays composed of 16.5 to 22.5 repeats (that bind to sites 18-24 bps in length preferably including a 5' T) should be made to ensure robust activity of TALE-activators.

Once a binding site has been identified using the methods described herein, the methods can further include generating a TALE-activator that binds to an identified binding site. The TALE activators include a TAL effector repeat array assembly (which binds to the identified binding site) fused to a transcription activator. Transcription activators that can be used in the TALE activators are known in the art, e.g., one or more, preferably four, VP16 peptides (i.e., VP64), or an NF-KB p65 transactivation domain. See, e.g., Tremblay et al., Hum Gene Ther. 2012 Aug; 23(8):883-90; Li et al., Scientific Reports 2:897 (2012) DOI: 10.1038/srep00897; and US 20110301073.

TAL effector repeat arrays include tandem repeats, typically 33-35 amino acids in length. Each repeat is largely identical except for two variable amino acids at positions 12 and 13, the repeat variable di-residues (RVDs). The C-terminal repeat is generally shorter and referred to as a "half repeat". Each repeat binds to a single base pair based on a simple code; the four most common RVDs each preferentially bind to one of the four bases (HD to C, NI to A, NG to T, NN to G) (see, e.g., Li et al., Scientific Reports 2:897 (2012); Boch et al., Review of Phytopathology 48: 419-36; US 20110301073). Thus, an engineered TALE-activator protein with N.5 domains will contact a site that is N.5+1.5 bps long (which includes the 5' T). For example, a TALE-activator protein as described herein that is 12.5 domains long will contact a 14 bp site including the 5' T if present, or a 13 bp site if the 5' T is absent.

A number of methods for TAL effector repeat array assembly are known in the art (e.g., REAL (Sander, J. D. et al. Nat Biotechnol 29, 697-698 (2011); Reyon, D. et al. Curr Protoc Mol Biol., 2012 October; Chapter 12: Unit 12.15); REAL-Fast (Reyon, D. et al. Curr Protoc Mol Biol., 2012 October; Chapter 12: Unit 12.15); or FLASH (Reyon, D. et al. Nat Biotechnol 30, 460-465 (2012) and PCT/US2012/046451)) and can be used to construct TALE-activators on the architecture used in this report. All plasmids required to practice REAL are available through the non-profit plasmid distribution service Addgene (addgene.org/talenginecring/). The archive of 376 plasmids required to practice FLASH and REAL-Fast are also available (TALengineering.org). Molecular biological techniques known in the art can be used to construct the TALE activators. See, e.g., Tremblay et al., Hum Gene Ther. 2012 Aug. 23(8):883-90; Li et al., Scientific Reports 2:897 (2012) DOI: 10.1038/srep00897; and US 20110301073.

DNase I Hypersensitive Sites

As used herein, a "DNase I hypersensitive site" is a short region of chromatin identified by its super sensitivity to cleavage by DNase I. DNase I hypersensitive sites can be identified using methods known in the art, e.g., empirically, or can be identified based on published data or databases of DNase I hypersensitive sites. For example, DNaseI fingerprinting can be performed by a method that includes DNaseI digestion of intact nuclei, isolating DNaseI double-hit' fragments as described in Sabo et al. (Nat Methods. 2006 Jul.;3(7):511-8.), and direct sequencing of fragment ends (which correspond to in vivo DNaseI cleavage sites) using the Illumina IIx (and Illumina HISEQ® by early 2011) platform (36 bp reads). Uniquely-mapping high-quality reads can be mapped to the genome using Bowtie. DNaseI sensitivity is directly reflected in raw tag density, which is shown in the track as density of tags mapping within a 150 bp sliding window (at a 20 bp step across the genome). DNaseI sensitive zones (HotSpots) can then be identified using the HotSpot algorithm described in Sabo et al. (Proc Natl Acad Sci USA. 2004 Nov. 30;101(48):16837-42). In some embodiments, false discovery rate thresholds of 1.0% (FDR 1.0%) are computed for each cell type by applying the HotSpot algorithm to an equivalent number of random uniquely-mapping 36mers. DNaseI hypersensitive sites (DHSs or Peaks) are then identified as signal peaks within FDR 1.0% hypersensitive zones using a peak-finding algorithm (I-max).

Other methods of identifying DNaseI hypersensitive sites can also be used. See, e.g., Madrigal and Krajewski, Front Genet. 2012; 3:230; Wu, Nature. 1980 Aug. 28; 286(5776): 854-60; Gross and Garrard, Annu Rev Biochem. 1988; 57:159-97; Boyle et al., Cell. 2008 Jan. 25; 132(2):311-22; McDaniell et al., Databases of DNaseI hypersensitive sites can also be used to identify and select candidate subsites, e.g., the DNase I hypersensitive regions identified in the University of Washington ENCODE data. Such sites can be identified using the UCSC genome browser (genome.ucsc.edu; Rosenbloom et al. Nucleic Acids Res 40, D912-917 (2012)).

In some embodiments, empirical DNase I sensitivity data obtained from a specific cell type of interest is used, i.e., the same cell type in which an increase in transcription is desired (i.e., the target cell type). In some embodiments, DNase I hypersensitive sites are selected that have been identified as DNase I hypersensitive sites in multiple different cell types, based on the reasoning that these areas have a high probability of being in open chromatin in the target cell type.

Computer- and Software-Based Embodiments

In some embodiments, various implementations of the systems and methods described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Figure 4:
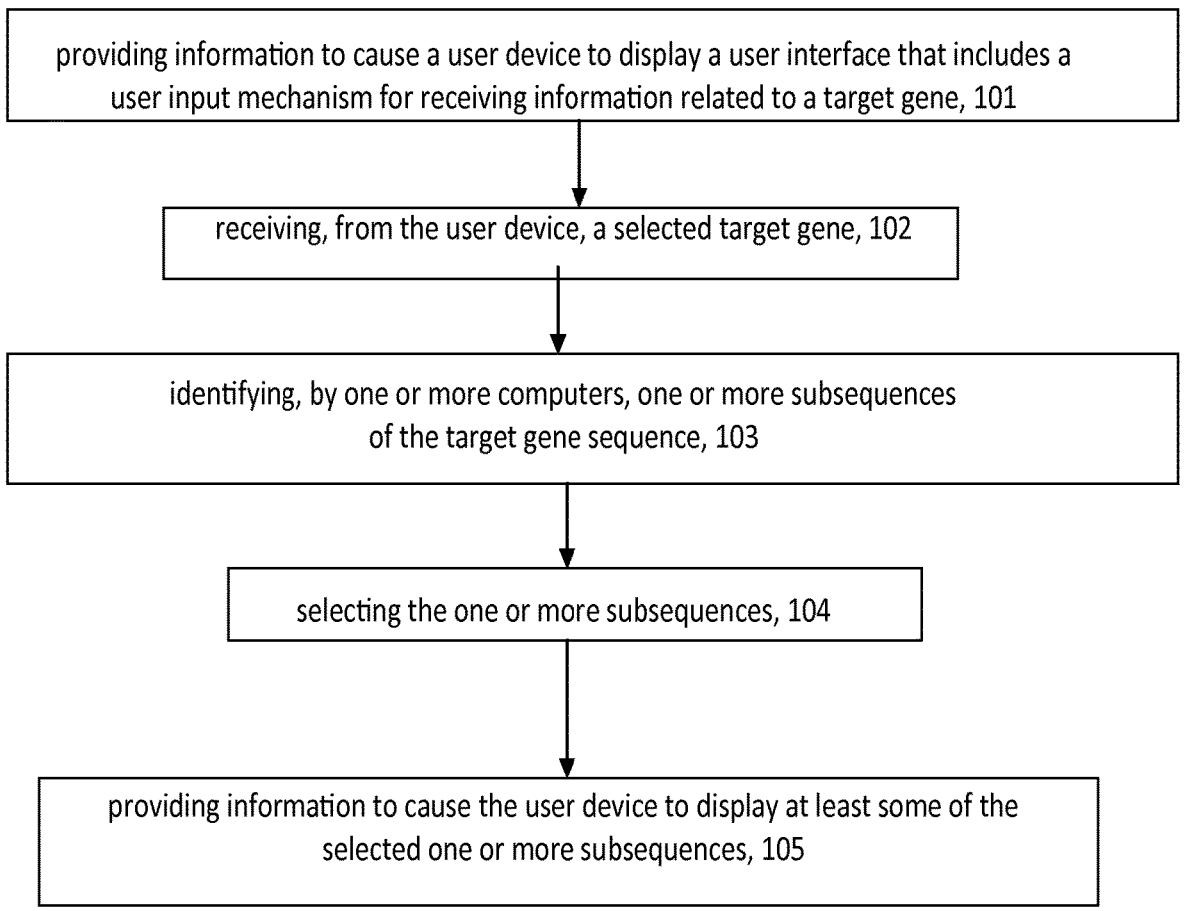
FIG. 4. A flowchart of an exemplary process for identifying potential TALE-activator binding sites.

In some embodiments, computer based identification of potential TALE-activator binding sites is performed as shown in FIG. 4. In some embodiments, the identification includes a comparison of a user-inputted query that includes a target sequence with records related to hypersensitive regions stored in a database. A computer system causes a user device to display a user interface that includes a user input mechanism for receiving information related to a target gene (101). A target sequence of interest, preferably a target sequence that is part of or comprises a regulatory region, e.g., a promoter, of a target gene, is provided by a user, e.g., by entry into a query box, to a computer processor programmed to perform the present methods. Regulatory regions can be identified using methods known in the art, e.g., from a database, or from empirical studies. The system receives the user-input query (102) (and optionally formats the query) and uses the query to select one or more records from a database. In some embodiments, the processor will identify DNase I hypersensitive regions within the target sequence based on comparison to records stored in one or more databases accessible by the computer system. In some alternative embodiments, the user will provide a target sequence already known to be in a DNase I hypersensitive region. In some embodiments, DNase I hypersensitive regions can be identified empirically, and the sequences entered into the computer.

Once a DNase I hypersensitive region has been identified, the processor will then identify potential TALE-activator binding sites within that region based on the guidelines set forth herein, i.e., TALE-activator binding sites composed of 16.5 to 22.5 repeats that bind to sites 18-24 bp in length (103). In some embodiments, users can change this length constraint, e.g., by entering a new value in a length input box. The modification of the length constraint input by the user can be received by the computer system as part of the original query definition or as a method to further filter a set of results provided based on a prior search. The studies of this report suggest that only TAL effector repeat arrays composed of 16.5 to 22.5 repeats (that bind to sites 18-24 bps in length) should be made to ensure robust activity of TALE-activators. The processor will then select one or more sequence of potential TALE-activator binding sites (104) and provide sequences of the identified potential TALE-activator binding sites to the user, e.g., by display on a screen, storage on a computer readable medium, or by inclusion in a message such as an email (105).

In some embodiments, the computer system is associated with a database that includes information required to generate a TALE-activator. Upon identification of a TALE-activator binding site, the software may access the additional stored information and provide users with access to the further information required to generate a TALE-activator, e.g., using FLASH or REAL/REAL-Fast. For example, in some embodiments, depending on the mode of assembly chosen (FLASH or REAL/REAL-Fast), the computer system will provide users with information about the names of plasmids required for assembly, and optionally a printable graphical guide. All plasmids required to practice REAL are available through the non-profit plasmid distribution service Addgene (addgene.org/talengineering/). The archive of 376 plasmids required to practice FLASH and REAL-Fast are also available (TALengineering.org).

Figure 5:
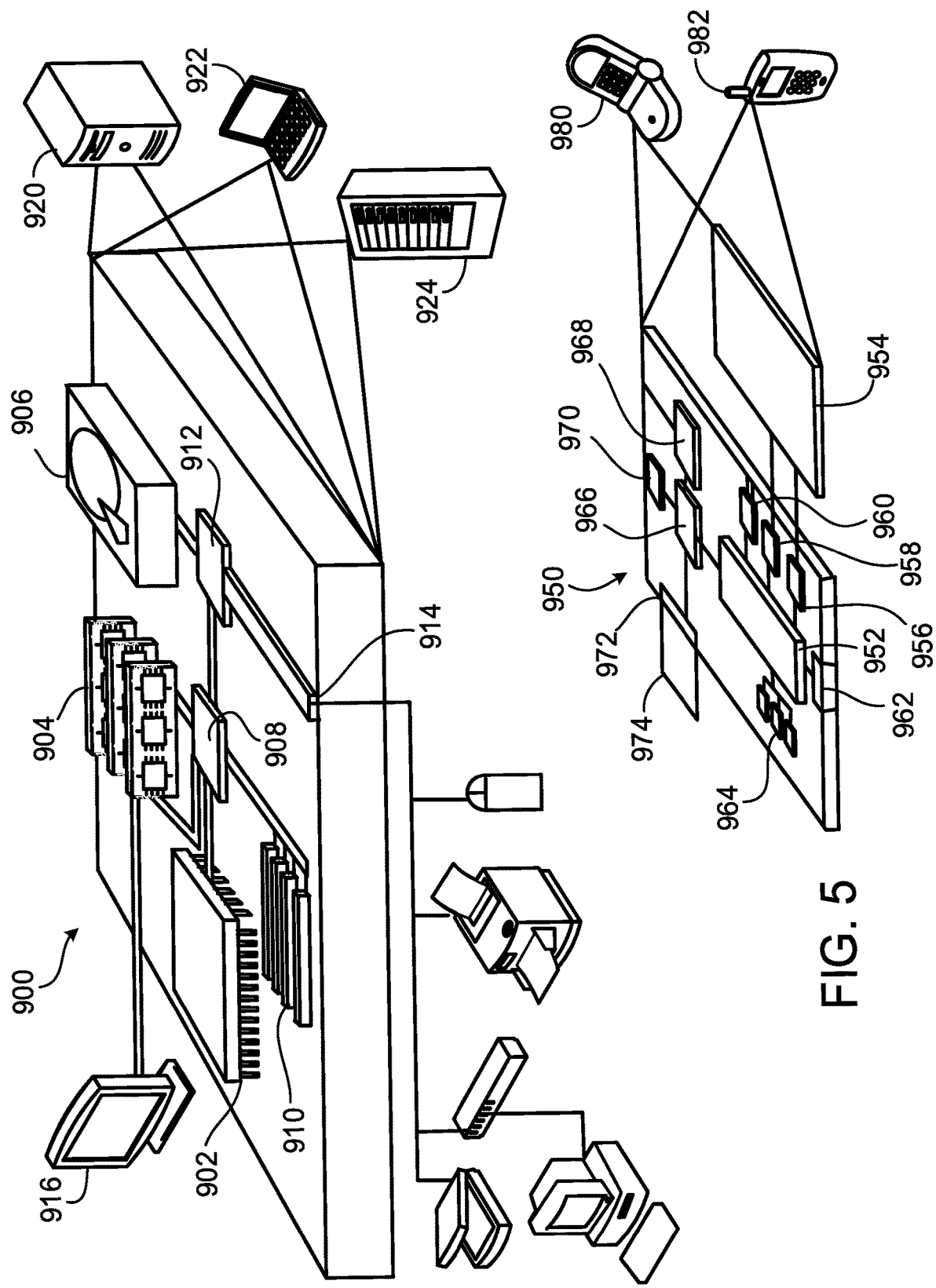
FIG. 5. An example of a computing device for use in the present methods.

FIG. 5 shows an example of a generic computer device 900 and a generic mobile computing device 950, which may be used with techniques described here. Computing device 900 is intended to represent various forms of digital computers, such as laptops, desktops, workstations, personal digital assistants, servers, blade servers, mainframes, and other appropriate computers. Computing device 950 is intended to represent various forms of mobile devices, such as personal digital assistants, cellular telephones, smartphones, and other similar computing devices. The components shown here, their connections and relationships, and their functions, are meant to be exemplary only, and are not meant to limit described and/or claimed implementations.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, memory on processor 902, or a propagated signal.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, BLUETOOTH®, ETHERNET®, wireless ETHERNET®) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provided in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 974 may also be provided and connected to device 950 through expansion interface 972, which may include, for example, a SIMM (Single In Line Memory Module) card interface. Such expansion memory 974 may provide extra storage space for device 950, or may also store applications or other information for device 950. Specifically, expansion memory 974 may include instructions to carry out or supplement the processes described above, and may include secure information also. Thus, for example, expansion memory 974 may be provided as a security module for device 950, and may be programmed with instructions that permit secure use of device 950. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 974, memory on processor 952, or a propagated signal that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a BLUETOOTH®, WiFi, or other such transceiver (not shown). In addition, GPS (Global Positioning System) receiver module 970 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smartphone 982, personal digital assistant, or other similar mobile device.

In addition to the steps described herein and shown in the figures, other steps may be provided, or steps may be eliminated, from the described flows, and other components may be added to, or removed from, the described systems. Accordingly, other embodiments are within the scope of the present invention.

Methods for Optimizing Expression Levels of Target Genes

At least three sources of variation exist in the various TALE-activator architectures described to date: (1) variability within TAL effector repeats of amino acids present at positions other than the hypervariable residues, (2) differences in the length and composition of the TAL effector-derived sequences that flank the TAL effector repeat array, and (3) the choice of activation domain used (e.g., VP16 or VP64). Boch and colleagues have recently presented data suggesting that variation in the amino acids at non-hypervariable repeat positions can affect binding activity (Streubel, J., et al. Nat Biotechnol 30, 593-595 (2012)). Various reports have also shown that differences in the length of TAL effector-derived sequences flanking the TAL effector repeat array can influence activities of TALE-activators (Miller, J. C. et al. Nat Biotechnol 29, 143-148 (2011); Zhang, F. et al. Nat Biotechnol 29, 149-153 (2011); Mussolino, C. et al. Nucleic Acids Res 39, 9283-9293 (2011)).

Described herein are a number of different approaches that can be used to fine-tune the level of gene expression induced by TALE-activators, an important capability that will broaden the range of applications for this technology.

First, varying the position of TALE-activator binding (even within a single DNase I hypersensitive site) can lead to differences in the level of activation observed. Although it is currently not possible to predict the level of activation induced from any given site, the high success rate and ease with which TALE-activators can be constructed using the present methods make it straightforward for one of skill in the art to produce a panel of TALE-activators of differing activities, and empirically identify activators that induce desired levels of expression.

Second, choosing DNA-binding domains composed of 16.5 to 22.5 TALE repeats as described herein is predicted to result in more highly active TALE activators.

Third, varying the activation domain can affect the level of gene expression induced by a TALE-activator. For example, in the two cell lines examined herein, VP64 TALE-activators generally induced higher levels of gene expression than matched counterparts bearing a p65 activation domain.

Finally, using combinations of TALE-activators can function synergistically to activate a target gene. Thus different combinations of TALE-activators can be tested to find the desired level of gene expression; in addition, these combinations can be used to make target genes responsive to multiple inputs, enabling synthetic biology applications in which artificial circuits interface with endogenous genes. In some embodiments, pairs (or more) of TALE activators that all target the same gene, but bind to different places in the regulatory region of the gene, are used. In some embodiments, all of the TALE activators have different transactivation domains, e.g., combinations of VP64 and p65 TALE-activators; in some embodiments, all of the TALE activators have the same transactivation domain. e.g., all either VP64 or p65 domains.

Methods for Regulating Expression of Non-Coding Genes

The present data demonstrate that TALE-activators can be used to regulate expression of a miRNA cluster, and thus might also be used to increase expression of other classes of non-coding genes such as lincRNAs, snoRNAs or piRNAs. Therefore in some embodiments the methods include selecting TALE-activator binding sites that are within regulatory regions of non-coding genes.

EXAMPLES

The invention is further described in the following examples, which do not limit the scope of the invention described in the claims.

Methods

The following methods were used in the experiments described in the Examples below.

Selection of TALE-activator binding sites. For the human VEGF-A gene, target sites were chosen that fall within DNase I hypersensitive sites previously described for 293 cells (Liu, P. Q. et al. J Biol Chem 276, 11323-11334 (2001)). For the NTF3 and miR-302/367 cluster genes, target sites were chosen within DNase I hypersensitive regions identified from University of Washington ENCODE data using the UCSC genome browser (genome.ucsc.edu; Rosenbloom, K. R. et al. Nucleic Acids Res 40, D912-917 (2012)); these regions were targeted because they have been identified as DNase I hypersensitive sites in multiple different cell types and therefore it was reasoned that these areas had a high probability of being in open chromatin.

Construction of TALE activators. DNA fragments encoding TAL effector repeat arrays were generated using the Fast Ligation-based Automatable High-throughput Assembly (FLASH) method as previously described (Reyon et al., 2012, and PCT/US2012/046451). These fragments were cloned using overhangs generated by digestion with BsmBI restriction enzyme into expression vectors containing an EF1α promoter and the Δ 152 N-terminal and +95 C-terminal TALE-derived domains from the previously described TALE-activator NT-L+95.[2] NF-KB p65 and VP64 activation domains were fused directly to the C-terminal end of the +95 domain and all fusion proteins harbor a nuclear localization signal.

Cell Culture and Transfection. Human Flp-In T-REx 293 cells and primary human BJ fibroblasts were maintained in Advanced DMEM supplemented with 10% FBS, 1% penicillin-streptomycin and 1% Glutamax (Life Technologies). Cells were transfected using either LIPOFECTAMINE® LTX (Life Technologies) or NUCLEOFECTION® (Lonza) according to manufacturer's instructions. Briefly, for experiments targeting VEGF-A and NTF3 expression, 160,000 Flp-In T-REx 293 cells were seeded in 24-well plates and transfected the following day with 300 ng of plasmid encoding TALE-activator, 30 ng of PMAXGFP® plasmid (Lonza), 0.5 μl Plus Reagent and 1.65 μl LIPOFECTAMINE® LTX. For experiments targeting miR-302/

367 cluster expression, 5×10⁵ BJ fibroblasts were Nucleofected with 10 μg of plasmid encoding TALE-activator and 500 ng of PMAXGFP® plasmid using the NHDF kit (Lonza) and program U-023 on the Nucicofector NUCLEOFECTOR® 2b device.

ELISA Assays. Flp-In TREx 293 cells were transfected with plasmids encoding TALE-activators targeted to the human VEGF-A gene. All transfections were performed in triplicate. Cell media was harvested 40 hours after transfection and secreted VEGF-A protein levels in the media were assayed using a Human VEGF-A ELISA kit (R&D Systems). All samples were measured according to the manufacturer's instructions. Fold-activation values were calculated by dividing mean VEGF-A levels from media harvested from cells transfected with plasmids expressing TALE-activators by mean VEGF-A levels from cells transfected with plasmid expressing only the VP64 or p65 activation domain.

Quantitative RT-PCR assays. To measure NTF3 mRNA levels, cells were harvested 2 days post-transfection and total RNA was isolated using the TRIZOL® Plus RNA purification system (Ambion). RNA was reverse transcribed using SUPERSCRIPT® III First-Strand Synthesis Super-Mix and oligo-dT primer (Life Technologies). qPCR was then performed using the following TAQMAN® primer/probe sets, as previously described[2] except with the modification that the GAPDH probe was labeled with HEX to allow for multiplexing -NTF3 forward primer: 5'-GATAAACACTGGAACTCTCAGTGCAA-3' (SEQ ID NO:52); NTF3 reverse primer: 5'-GCCAGCCCACGAGTTTATTGT-3' (SEQ ID NO:53); NTF3 TAQMAN® probe: 5'-/56-FAM/CAAACCTAC/ZEN/GTCCGAGCACT-GACTTCAGA/3IABkFQ/-3' (SEQ ID NO:54); GAPDH forward primer: 5'-CCATGTTCGTCATGGGTGTGA-3' (SEQ ID NO:55); GAPDH reverse primer: 5'-CATGGACTGTGGTCATGAGT-3' (SEQ ID NO:56); GAPDH TAQMAN® probe: 5'-/5HEX/TCCTGCACC/ZEN/ACCAACT-GCTTAGCA/ 3IABkFQ/-3' (SEQ ID NO:57). All TALE-activator-encoding plasmids and control plasmids were introduced into cells by NUCLEOFECTION® in triplicate and qRT-PCR was performed in triplicate on each sample.

To measure miR-302a transcript levels, cells were harvested 3 days post-transfection and GFP-positive cells were isolated by flow cytometry. Total miRNA was isolated using the mirVana miRNA Isolation Kit (Ambion). Reverse transcription and qPCR were performed according to manufacturer's instructions using Applied Biosystems TAQMAN® microRNA Assays (cat. #000529 for has-miR-302a and cat. #001006 for RNU48 control). Fold-activation of miR-302a RNA transcripts was calculated by comparing transcript levels from BJ fibroblasts transfected with plasmids encoding TALE-activators to transcript levels from BJ fibroblasts transfected with control plasmids expressing only the VP64 or p65 activation domains and using the comparative $C_T$ ($\Delta\Delta C_T$) method. All TALE-activators and controls were introduced into cells by NUCLEOFECTION® in triplicate and qRT-PCR for miR302a transcript and small RNA control RNU48 were performed in triplicate on each sample.

Example 1

Figure 1B:
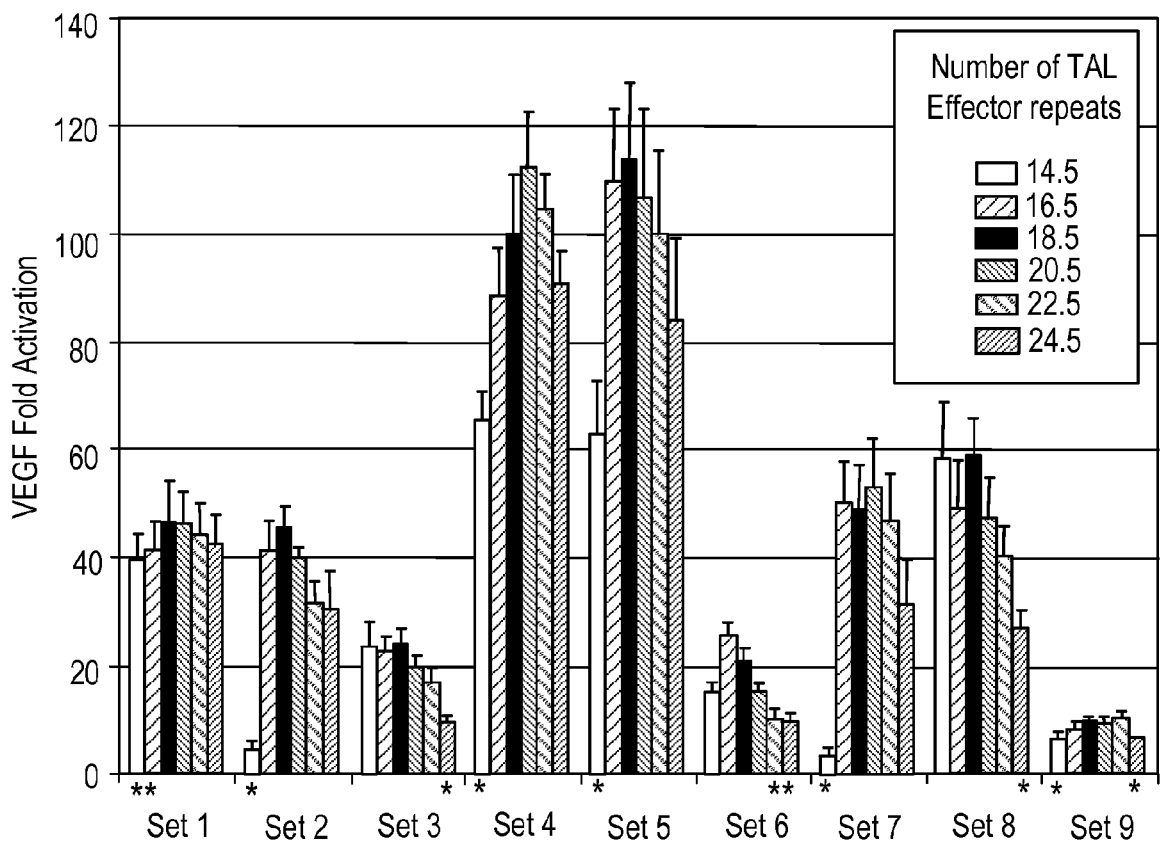
Figure 1C:
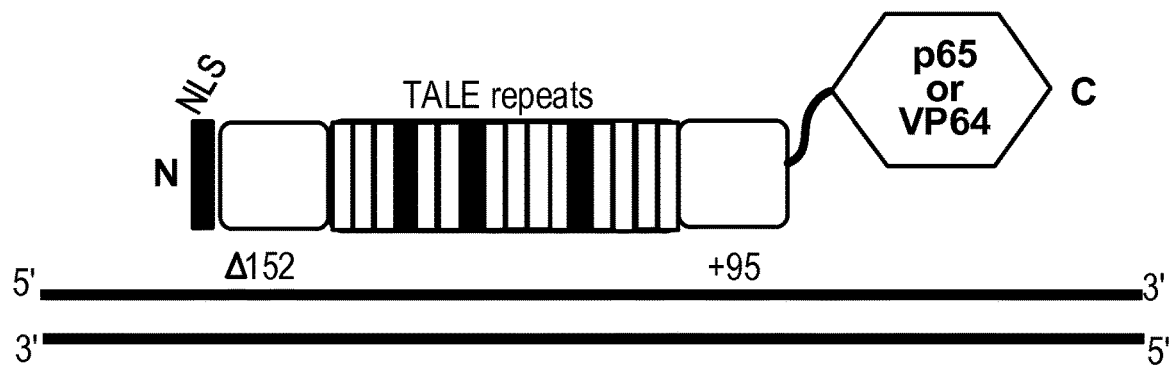
FIG. 1C Schematic of TALE-activator architecture used in this study. The TALE-activator architecture we used for our experiments is similar to one described by Rebar and colleagues (Miller, J. C. et al. Nat Biotechnol 29, 143-148 (2011)). These proteins contain the Δ152 N-terminal domain and the +95 C-terminal domain that flank the TAL effector repeat array as well as an N-terminal nuclear localization signal (NLS) and a C-terminal activation domain (either VP64 or p65).

In initial experiments, a systematic and large-scale study aimed at defining the number of TAL effector repeats needed for optimal TALE-activator function was performed. A single consistent architecture based on one previously used by Rebar and colleagues to build a highly active TALE-activator (Miller, J. C. et al. Nat Biotechnol 29, 143-148 (2011)) (FIG. 1C), but that harbors a VP64 activation domain, was utilized. Using the recently described Fast Ligation-based Automatable Solid-phase High-throughput (FLASH) assembly method (Reyon, D. et al. Nat Biotechnol 30, 460-465 (2012) and PCT/US2012/046451), sets of six variable-length TALE-activators (harboring arrays of 14.5, 16.5, 18.5, 20.5, 22.5, or 24.5 TAL effector repeats) were constructed for nine different target regions within the human VEGF-A gene (a total of 54 TALE-activators). To minimize the effects of potentially obstructive chromatin on our experiment, the nine regions chosen all lie within a single DNase I hypersensitive region located ~500 bp downstream of the VEGF-A transcription startpoint (FIG. 1a). Strikingly, 53 out of the 54 TALE-activators tested induced significant increases in VEGF-A protein expression in cultured human cells ranging from 5.3- to 114-fold (average of 44.3-fold activation) (FIG. 1b). Interestingly, for each of the nine target regions, either the 14.5 repeat and/or 24.5 repeat TALE-activators showed significantly lower fold-activation of VEGF-A than the other proteins harboring 16.5 to 22.5 repeats (FIG. 1b). These data suggest that the DNA-binding activities of monomeric TALE-activators can be optimized by ensuring that they contain at least 16.5, but no more than 22.5, repeats.

Figure 2A:
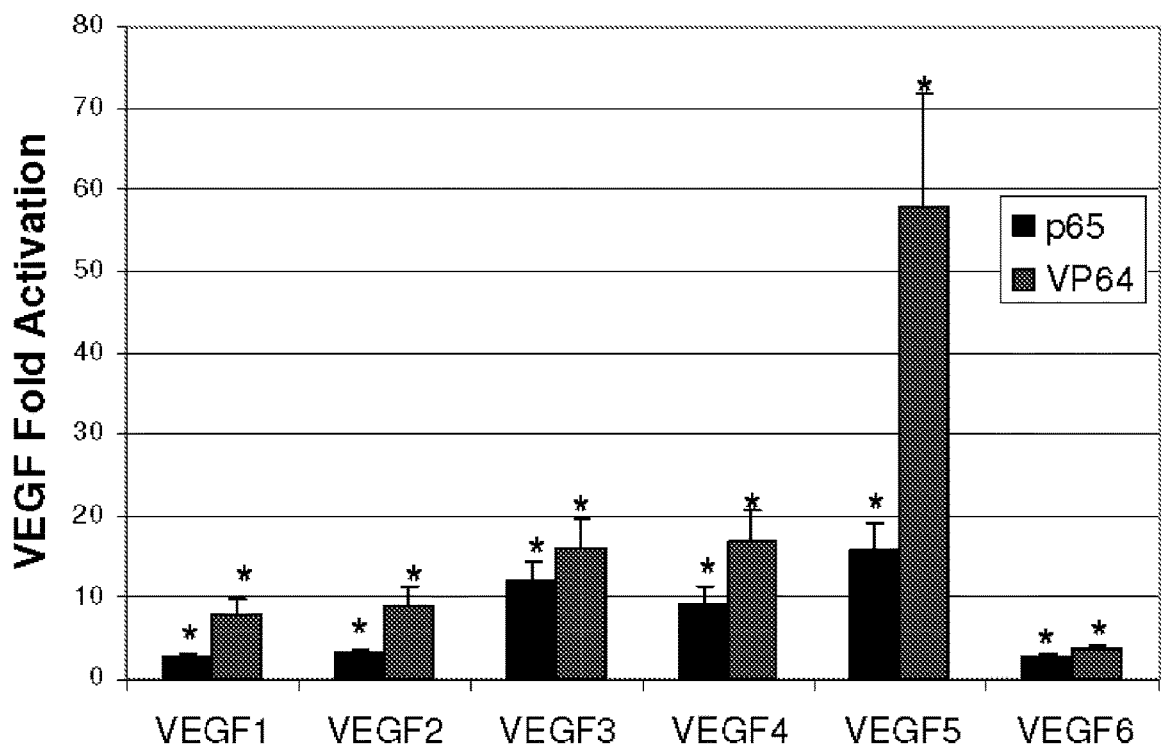
FIGS. 2A-C Activities of 16 TALE-activators targeted to the endogenous human VEGF-A, miR-302/367 cluster, and NTF3 genes. For all three gene targets, experiments were performed in triplicate with TALE-activators harboring either the VP64 (gray bars) or NF-KB p65 (black bars) activation domain. Error bars represent standard errors of the mean. (a) VEGF-A-targeted TALE-activators. Fold-activation values of VEGF-A protein were determined as described in Methods. Asterisks indicate activators that induced fold-activation of VEGF-A significantly greater than 1, as determined by a one-sided, paired t-test. (b) miR-302/367-targeted TALE-activators. Fold-activation values of miR-302 a transcript were determined as described in Methods. Asterisks indicate activators that induced fold-activation of miR-302a transcript levels to a level significantly greater than 1 as determined by a one-sided, paired t-test. (c) NTF3-targeted TALE activators. Expression levels of NTF3 mRNA relative to GAPDH mRNA are shown. Asterisks indicate activators that induced significant elevation of NTF3 transcript levels relative to a control as determined by a one-sided, paired t-test.
Figure 2B:
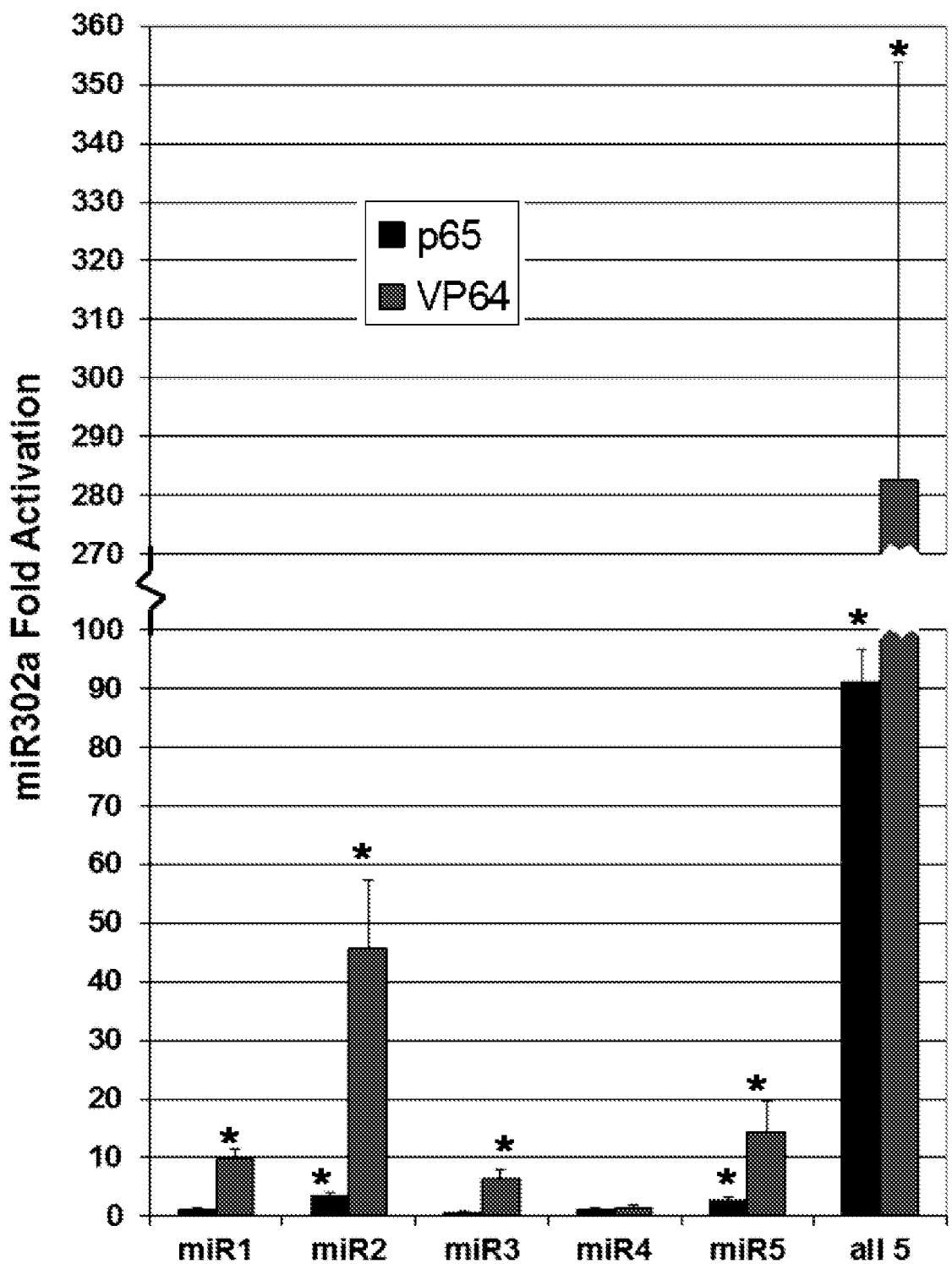
Figure 2C:
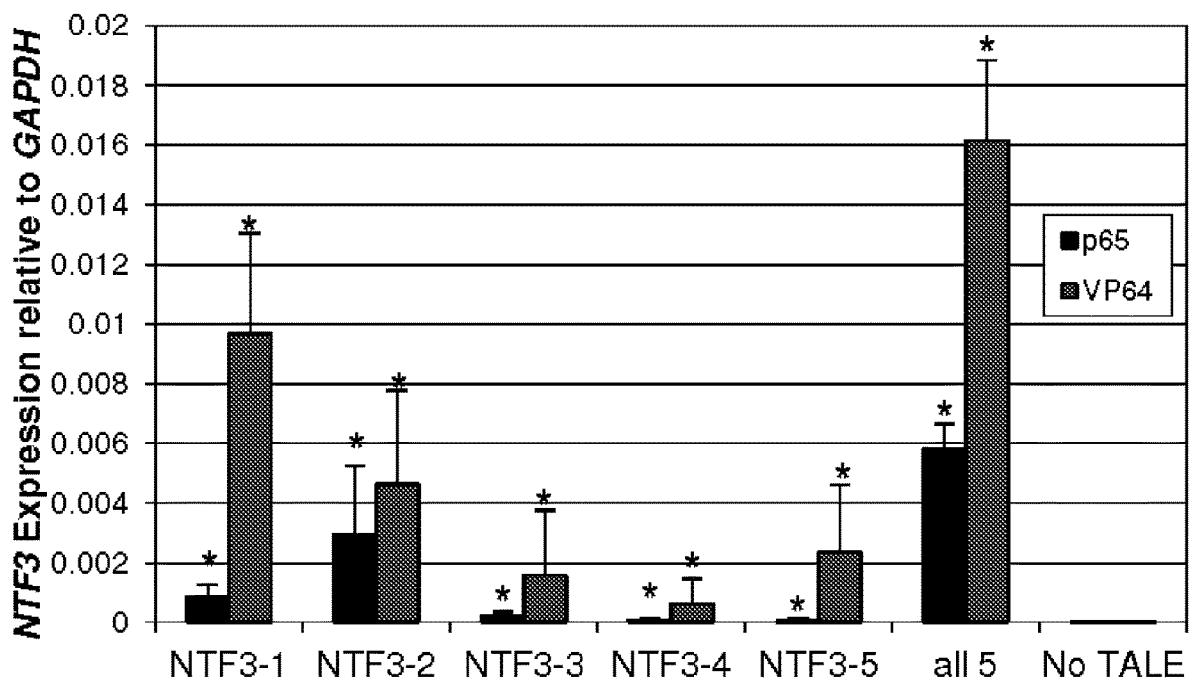
Figure 2D:
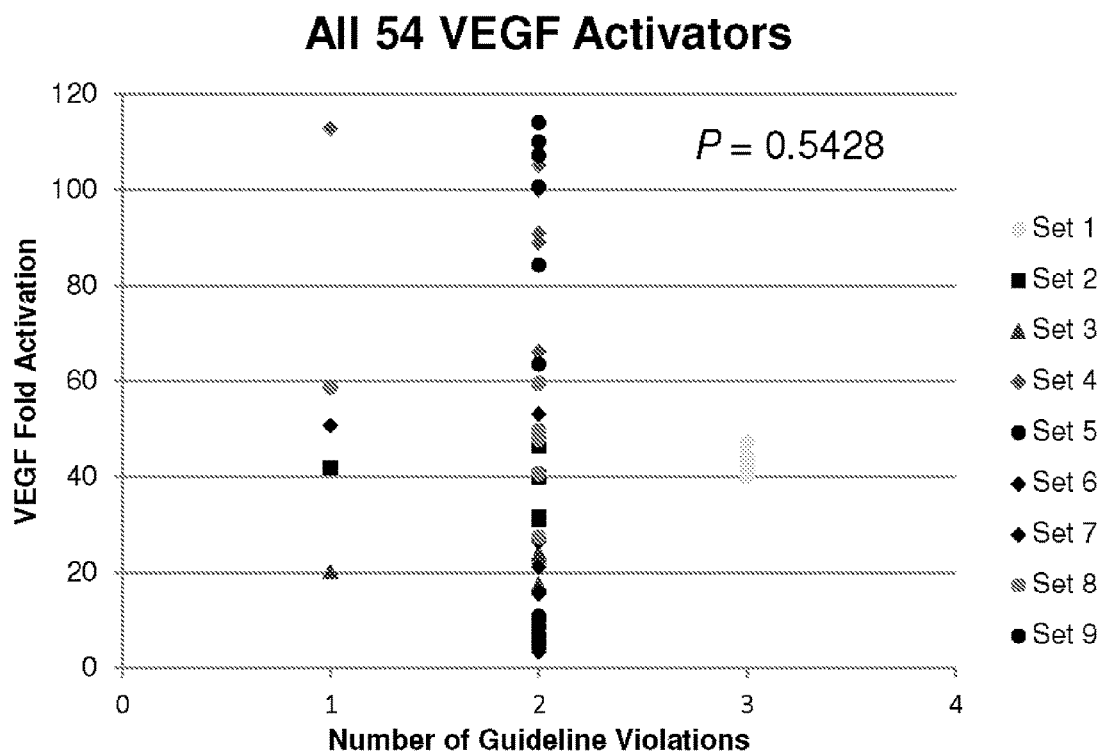
FIGS. 2D-E Correlation between activity of TALE-activators and violations of previously described computationally-derived target site guidelines. (d) Guideline violations and activities of 54 TALE-activators targeted to the human VEGF-A gene. Correlation p-value is shown. (e) Same data as in (d) but broken down into nine sets each consisting of six TALE-activators composed of 14.5, 16.5, 18.6, 20.5, 22.5 or 24.5 TAL effector repeat arrays targeted to overlapping sites.
Figure 2E:
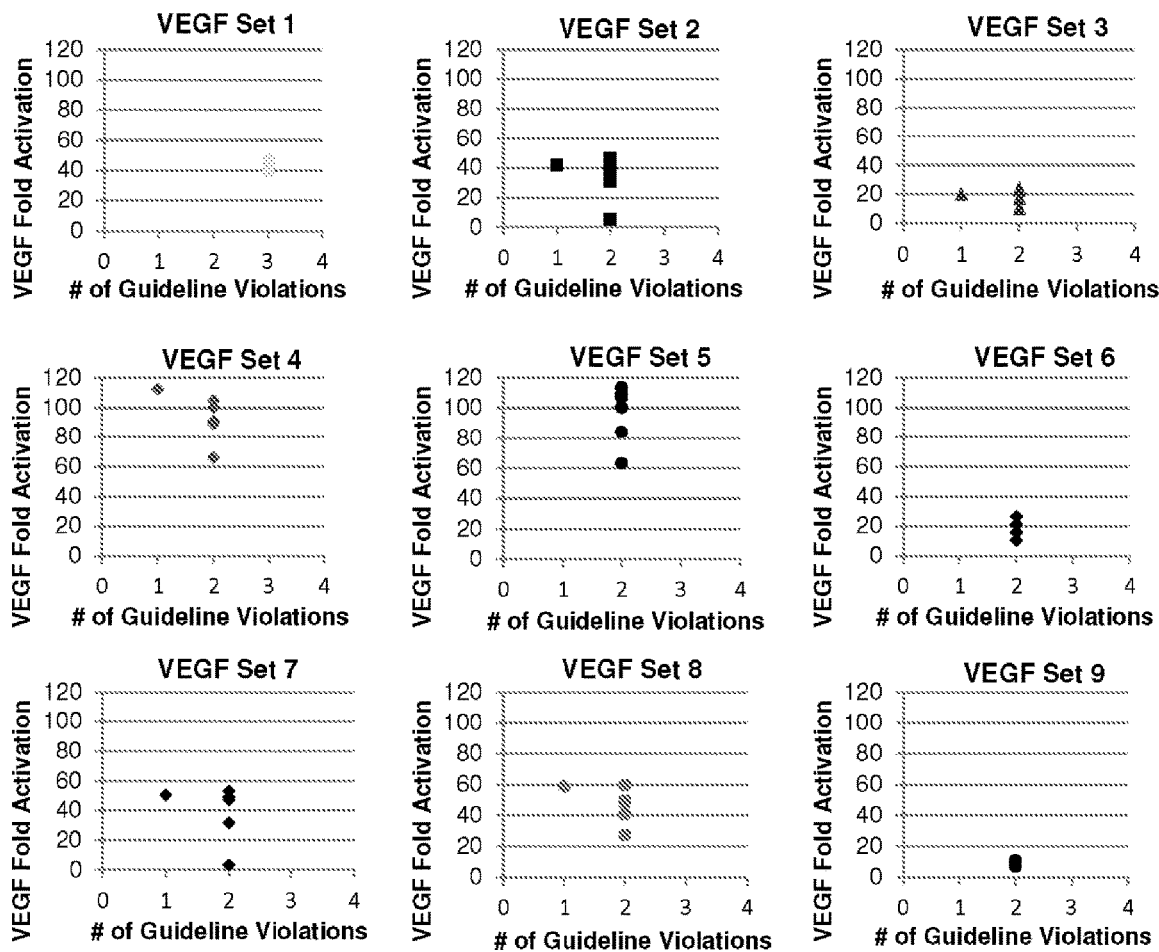

The data on the activities of the 54 VEGF-A-targeted TALE-activators was used to test the importance of following five computationally-derived guidelines for target site choice (Doyle, E. L. et al. Nucleic Acids Res 40, W117-122 (2012)). All 54 sites targeted failed to meet one or more of these five guidelines with 49 of the 54 sites actually violating two or more guidelines (note that all of the sites did meet the guideline requiring a 5' T) (Table 3). The ability of 53 of the 54 activators tested to increase VEGF-A expression by five-fold or more clearly demonstrates that there is no absolute requirement to follow at least four of the five design guidelines. Whether a relationship might exist between the total number of guideline violations and the level of TALE-activator activity observed was examined, but no significant correlation was found (p=0.5428; FIG. 2D). Instead, the level of fold-activation induced appeared to be largely locus-associated—that is, TALE-activators of variable lengths targeted to one of the nine loci, regardless of the number of guideline violations, tend to show similar levels of fold-activation (FIG. 2E). Thus highly active monomeric TALE-activators can be made without meeting four of the five design guidelines. The ability to relax these restrictions improved the targeting range of TALE-activators by more than ten-fold—for example, enabling proteins consisting of 16.5 TAL effector repeats to be made for a site once in every two bps of random DNA sequence.

TABLE 3

| TALE Name | Target site | SEQ ID NO: | Guidelines | | | | | Total Guideline Violations |
|---|---|---|---|---|---|---|---|---|
| | | | 1 | 2 | 3 | 4 | 5 | |
| VEGF1 | TCGGGAGGCGCAGCGGTT | 58. | | | | | X | 1 |
| VEGF2 | TTGGGGCAGCCGGGTAGC | 59. | | X | | X | X | 3 |

TABLE 3-continued

| TALE Name | Target site | SEQ ID NO: | Guidelines 1 | 2 | 3 | 4 | 5 | Total Guideline Violations |
|---|---|---|---|---|---|---|---|---|
| VEGF3 | TGGAGGGGGTCGGGGCTC | 60. | | | | X | X | 2 |
| VEGF4 | TGAGTGACCTGCTTTTGGG | 61. | | | X | X | X | 3 |
| VEGF5 | TGAGTGAGTGTGTGCGTGT | 62. | | | X | | X | 2 |
| VEGF6 | TCACTCCAGGATTCCAATA | 63. | | | X | X | | 2 |
| Ntf3-1 | TTCTGTTCACGGGACTCA | 64. | | X | | X | | 2 |
| Ntf3-2 | TCCGAACAGCTCCGCGCA | 65. | | | | X | | 1 |
| Ntf3-3 | TTCCCCTGCTGGGTAGTG | 66. | | X | | X | X | 3 |
| Ntf3-4 | TACGCCTCAGACCTGATC | 67. | | | | X | | 1 |
| Ntf3-5 | TCCCTCAATCTGGGAAAG | 68. | | | | X | | 1 |
| miR1 | TGGAAGCAATCTATTTAT | 69. | | | | | | 0 |
| miR2 | TACATTTAACATGTAGAT | 70. | | | | | | 0 |
| miR3 | TAGAAACACAATGCCTTT | 71. | | | | | | 0 |
| miR4 | TGGGAGCACTCATTGTTA | 72. | | | | X | X | 2 |
| miR5 | TAATCTATGCCATCAAAC | 73. | | | X | X | | 2 |
| VEGF1-1 | TTGGGGGTGACCGCCG | 74. | | X | | X | X | 3 |
| VEGF1-2 | TTGGGGGTGACCGCCGGA | 75. | | X | | X | X | 3 |
| VEGF1-3 | TTGGGGGTGACCGCCGGAGC | 76. | | X | | X | X | 3 |
| VEGF1-4 | TTGGGSGTGACCGCCGGAGCGC | 77. | | X | | X | X | 3 |
| VEGF1-5 | TTGGGGGTGACCGCCGGAGCGCGG | 78. | | X | | X | X | 3 |
| VEGF1-6 | TTGGGGGTGACCGCCGGAGCGCGGCG | 79. | | X | | X | X | 3 |
| VEGF2-1 | TCCCGCAGCTGACCAG | 80. | | | | X | X | 2 |
| VEGF2-2 | TCCCGCAGCTGACCAGTC | 81. | | | | X | | 1 |
| VEGF2-3 | TCCCGCAGCTGACCAGTCGC | 82. | | | | X | X | 2 |
| VEGF2-4 | TCCCGCAGCTGACCAGTCGCGC | 83. | | | | X | X | 2 |
| VEGF2-5 | TCCCGCAGCTGACCAGTCGCGCTG | 84. | | | | X | X | 2 |
| VEGF2-6 | TCCCGCAGCTGACCAGTCGCGCTGAC | 85. | | | | X | X | 2 |
| VEGF3-1 | TACCACCTCCTCCCCG | 86. | | | | X | X | 2 |
| VEGF3-2 | TACCACCTCCTCCCCGGC | 87. | | | | X | X | 2 |
| VEGF3-3 | TACCACCTCCTCCCCGGCCG | 88. | | | | X | X | 2 |
| VEGF3-4 | TACCACCTCCTCCCCGGCCGGC | 89. | | | | X | | 1 |
| VEGF3-5 | TACCACCTCCTCCCCGGCCGGCGG | 90. | | | | X | X | 2 |
| VEGF3-6 | TACCACCTCCTCCCCGGCCGGCGGCG | 91. | | | | X | X | 2 |
| VEGF4-1 | TCCCCGGCCGGCGGCG | 92. | | | | X | X | 2 |
| VEGF4-2 | TCCCCGGCCGGCGGCGGA | 93. | | | | X | X | 2 |
| VEGF4-3 | TCCCCGGCCGGCGGCGGACA | 94. | | | | X | X | 2 |
| VEGF4-4 | TCCCCGGCCGGCGGCGGACAGT | 95. | | | | | X | 1 |
| VEGF4-5 | TCCCCGGCCGGCGGCGGACAGTGG | 96. | | | | X | X | 2 |

TABLE 3-continued

| TALE Name | Target site | SEQ ID NO: | Guidelines 1 | 2 | 3 | 4 | 5 | Total Guideline Violations |
|---|---|---|---|---|---|---|---|---|
| VEGF4-6 | TCCCCGGCCGGCGGCGGACAGTGGAC | 97. | | | | X | X | 2 |
| VEGF5-1 | TGGACGCGGCGGCGAG | 98. | | | | X | X | 2 |
| VEGF5-2 | TGGACGCGGCGGCGAGCC | 99. | | | | X | X | 2 |
| VEGF5-3 | TGGACGCGGCGGCGAGCCGC | 100. | | | | X | X | 2 |
| VEGF5-4 | TGGACGCGGCGGCGAGCCGCGG | 101. | | | | X | X | 2 |
| VEGF5-5 | TGGACGCGGCGGCGAGCCGCGGGC | 102. | | | | X | X | 2 |
| VEGF5-6 | TGGACGCGGCGGCGAGCCGCGGGCAG | 103. | | | | X | X | 2 |
| VEGF6-1 | TCCCAAGGGGAGGGC | 104. | | | | X | X | 2 |
| VEGF6-2 | TCCCAAGGGGAGGGCTC | 105. | | | | X | X | 2 |
| VEGF6-3 | TCCCAAGGGGAGGGCTCAC | 106. | | | | X | X | 2 |
| VEGF6-4 | TCCCAAGGGGAGGGCTCACGC | 107. | | | | X | X | 2 |
| VEGF6-5 | TCCCAAGGGGAGGGCTCACGCCG | 108. | | | | X | X | 2 |
| VEGF6-6 | TCCGAAGGGGAGGGCTCACGCCGGG | 109. | | | | X | X | 2 |
| VEGF7-1 | TCCGTCAGCGCGACTG | 110. | | | | X | X | 2 |
| VEGF7-2 | TCCGTCAGCGCGACTGGT | 111. | | | | | X | 1 |
| VEGF7-3 | TCCGTCAGCGCGACTGGTCA | 112. | | | | X | X | 2 |
| VEGF7-4 | TCCGTCAGCGCGACTGGTCAGC | 113. | | | | X | X | 2 |
| VEGF7-5 | TCCGTCAGCGCGACTGGTCAGCTG | 114. | | | | X | X | 2 |
| VEGF7-6 | TCCGTCAGCGCGACTGGTCAGCTGCG | 115. | | | | X | X | 2 |
| VEGF8-1 | TCCACTGTCCGCCGCC | 116. | | | | X | | 1 |
| VEGF8-2 | TCCACTGTCCGCCGCCGG | 117. | | | | X | X | 2 |
| VEGF8-3 | TCCACTGTCCGCCGCCGGCC | 118. | | | | X | X | 2 |
| VEGF8-4 | TCCACTGTCCGCCGCCGGCCGG | 119. | | | | X | X | 2 |
| VEGF8-5 | TCCACTGTCCGCCGCCGGCCGGGG | 120. | | | | X | X | 2 |
| VEGF8-6 | TCCACTGTCCGCCGCCGGCCGGGGA | 121. | | | | X | X | 2 |
| VEGF9-1 | TCCACCCCGCCTCCGG | 122. | | | | X | X | 2 |
| VEGF9-2 | TCCACCCCGCCTCCGGGC | 123. | | | | X | X | 2 |
| VEGF9-3 | TCCACCCCGCCTCCGGGCGC | 124. | | | | X | X | 2 |
| VEGF9-4 | TCCACCCCGCCTCCGGGCGCGG | 125. | | | | X | X | 2 |
| VEGF9-5 | TCCACCCCGCCTCCGGGCGCGGGC | 126. | | | | X | X | 2 |
| VEGF9-6 | TCCACCCCGCCTCCGGGCGCGGGCT | 127. | | | | X | X | 2 |

Figure 3A:
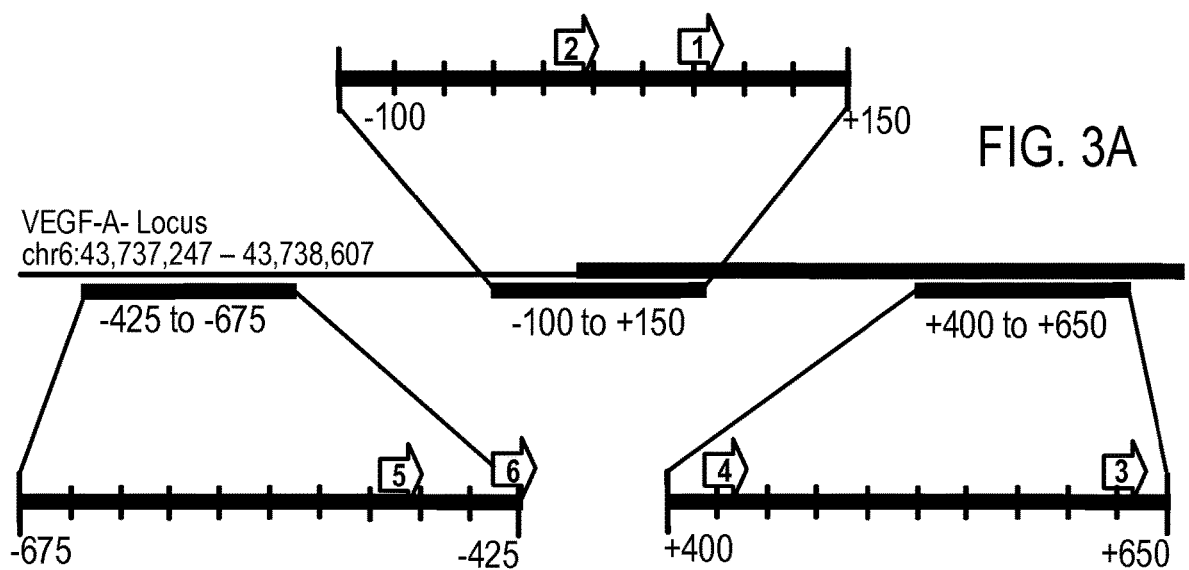
FIGS. 3A-C Schematic overview of TALE-activator binding sites within the (a) VEGF-A, (b) miR-302/367, and (c) NTF3 gene promoter regions. Thick black lines indicate exons, thin black lines indicate introns or promoter regions, and black arrows indicate the start site of transcription. Arrows labeled with miR1-miR5 represent miRNAs. Grey bars indicate digital DNAse I hypersensitive regions. DNAse I hypersensitive regions we targeted are expanded and red-arrows depict precise locations of TALE-activator binding sites and orientations of the activators when bound on the DNA (the arrow indicates the direction of the protein from amino- to carboxy-terminus when bound to its target DNA site).
Figure 3B:
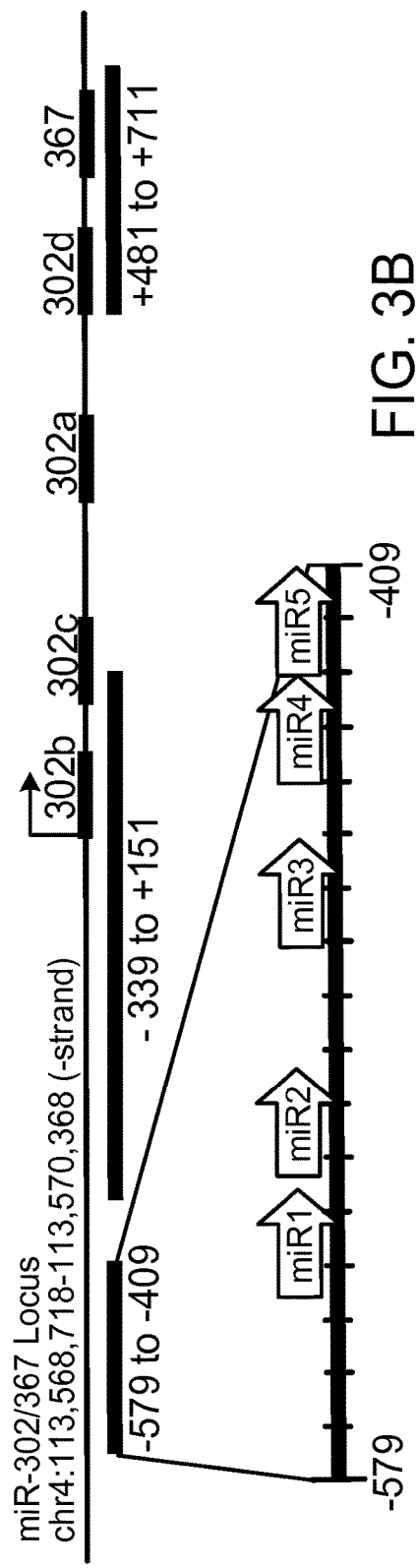
Figure 3C:
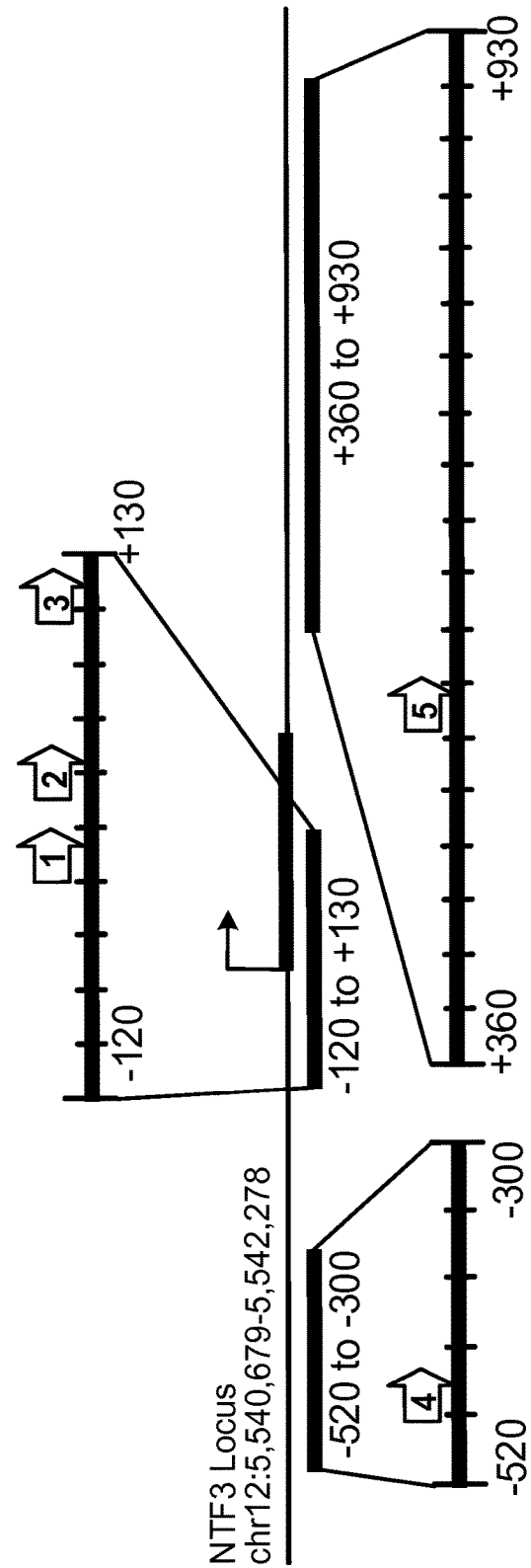

Having defined optimum repeat array lengths and relaxed criteria for choosing target sequences, whether TALE-activators made using these parameters would efficiently regulate expression of both protein-coding and miRNA genes in human cells was tested. For these experiments, FLASH was used to construct VP64 TALE-activators composed of 16.5 or 17.5 TAL effector repeats to six additional sites in the human VEGF-A gene promoter, to five sites in the human NTF3 gene promoter, and to five sites in the miR-302/367 cluster promoter. To minimize the potential confounding effects of obstructive chromatin, all 16 sites targeted were again chosen based on their position within cell-type-specific or database-predicted DNase I hypersensitivity regions (FIGS. 3A-B and Methods). Testing of these VP64 TALE-activators in human cells revealed that 15 of the 16 proteins induced significant increases in expression of their endogenous gene targets, an overall success rate of ~94% (FIGS. 2A-C, lighter grey bars). Notably, five of six TALE-activators targeted to VEGF-A and four of five activators targeted to the miR-302/367 cluster increased expression of their target genes by five-fold or more in human transformed 293 and primary BJ fibroblasts, respectively (FIGS. 2a and 2b). Because NTF3 mRNA is expressed at an essentially undetectable level in the 293 cells used for our experiments, it was not possible to reliably quantify fold-activation values for proteins targeted to this gene, but even the weakest activator induced an approximately 1000-fold increase in expression (FIG. 2c). Interestingly, replacement of VP64 with the NF-KB p65 activation domain led to decreased activation for all 15 functional activators (FIG. 2A-C, darker grey bars). These results demonstrate that VP64 TALE-activators composed of 16.5 to 17.5 repeats can robustly activate expression of endogenous human genes (including non-coding miRNA genes) without the need to follow restrictive targeting guidelines and that VP64 TALE-activators generally have stronger stimulatory effects than NF-KB p65 TALE-activators.

Because the present platform provides the capability to robustly generate multiple highly active TALE-activators for essentially any gene, the next experiments were performed to determine whether these proteins could also function synergistically. Activators are said to function synergistically if the fold-activation observed in the presence of multiple proteins is higher than the additive effects of the individual proteins. Naturally occurring activators in eukaryotes function synergistically (Carey, M. et al. Nature 345, 361-364 (1990)) and exploit this property to enable both combinatorial and graded control of transcription. To test whether TALE-activators might also behave synergistically, combinations of five VP64 or five p65 TALE-activators were tested on activation of the miR-302/267 cluster and the NTF3 gene. For all combinations tested, the expression of multiple activators led to substantially elevated transcription of the miR-302/367 and NTF3 genes (FIGS. 2b and 2c). Synergistic activation was observed with VP64 and p65 activators on the miR-302/367 cluster (FIG. 2b) and with p65 activators on the NTF3 gene (FIG. 2c). Thus, both VP64 and p65 TALE-activators can function synergistically to increase expression of endogenous human genes and this mechanism can be used to induce even greater levels of activation than can be achieved with individual activators.

REFERENCES

1. Mussolino, C. & Cathomen, T. TALE nucleases: tailored genome engineering made easy. *Curr Opin Biotechnol* (2012).
2. Miller, J. C. et al. A TALE nuclease architecture for efficient genome editing. *Nat Biotechnol* 29, 143-148 (2011).
3. Zhang, F. et al. Efficient construction of sequence-specific TAL effectors for modulating mammalian transcription. *Nat Biotechnol* 29, 149-153 (2011).
4. Geissler, R. et al. Transcriptional activators of human genes with programmable DNA-specificity. *PLoS One* 6, e19509 (2011).
5. Garg, A., Lohmueller, J. J., Silver, P. A. & Armel, T. Z. Engineering synthetic TAL effectors with orthogonal target sites. *Nucleic Acids Res* (2012).
6. Tremblay, J. P., Chapdelaine, P., Coulombe, Z. & Rousseau, J. TALE proteins induced the expression of the frataxin gene. *Hum Gene Ther* (2012).
7. Wang, Z. et al. An Integrated Chip for the High-Throughput Synthesis of Transcription Activator-like Effectors. *Angew Chem Int Ed Engl* 51, 8505-8508 (2012).
8. Cong, L., Zhou. R., Kuo, Y. C., Cunniff, M. & Zhang, F. Comprehensive interrogation of natural TALE DNA-binding modules and transcriptional repressor domains. *Nat Commun* 3, 968 (2012).
9. Bultmann, S. et al. Targeted transcriptional activation of silent oct4 pluripotency gene by combining designer TALEs and inhibition of epigenetic modifiers. *Nucleic Acids Res* 40, 5368-5377 (2012).
10. Cermak, T. et al. Efficient design and assembly of custom TALEN and other TAL effector-based constructs for DNA targeting. *Nucleic Acids Res* 39, e82 (2011).
11. Blancafort. P., Segal, D. J. & Barbas, C. F., 3rd Designing transcription factor architectures for drug discovery. *Mol Pharmacol* 66, 1361-1371 (2004).
12. Doyle, E. L. et al. TAL Effector-Nucleotide Targeter (TALE-NT) 2.0: tools for TAL effector design and target prediction. *Nucleic Acids Res* 40, W117-122 (2012).
13. Reyon, D. et al. FLASH assembly of TALENs for high-throughput genome editing. *Nat Biotechnol* 30, 460-465 (2012).
14. Carey, M., Lin, Y. S., Green, M. R. & Ptashne, M. A mechanism for synergistic activation of a mammalian gene by GAL4 derivatives. *Nature* 345, 361-364 (1990).
15. Sander, J. D. et al. Targeted gene disruption in somatic zebrafish cells using engineered TALENs. *Nat Biotechnol* 29, 697-698 (2011).
16. Reyon, D., Khayter, C., Regan, M. R., Joung, J. K. & Sander, J. D. Engineering Designer Transcription Activator-Like Effector Nucleases (TALENs). *Curr Protoc Mol Biol.*, Curr Protoc Mol Biol. 2012 October; Chapter 12: Unit 12.15.
17. Streubel, J., Blucher, C., Landgraf, A. & Boch, J. TAL effector RVD specificities and efficiencies. *Nat Biotechnol* 30, 593-595 (2012).
18. Mahfouz, M. M. et al. Targeted transcriptional repression using a chimeric TALE-SRDX repressor protein. *Plant Mol Biol* 78, 311-321 (2012).
19. Liu, P. Q. et al. Regulation of an endogenous locus using a panel of designed zinc finger proteins targeted to accessible chromatin regions. Activation of vascular endothelial growth factor A. *J Biol Chem* 276, 11323-11334 (2001).
20. Rosenbloom, K. R. et al. ENCODE whole-genome data in the UCSC Genome Browser: update 2012. *Nucleic Acids Res* 40, D912-917 (2012).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing transcription of a target gene sequence in a human cell, the method comprising
contacting the human cell with a fusion protein, wherein the fusion protein comprises
a DNA-binding domain comprising a transcription activator-like effector (TALE) repeat array that binds specifically to a subsequence of the target gene sequence, and a transactivation domain that increases transcription of the target gene sequence, wherein the subsequence is within a DNase I hypersensitive region of a regulatory region of the target gene sequence;
wherein the subsequence is 18-24 nucleotides long;
wherein the first nucleotide of the subsequence is a thymine;
wherein the second nucleotide of the subsequence is an adenine; and
wherein the base composition percentage of the subsequence is other than 0-63% adenine, 11-63% cytosine, 0-25% guanine, or 2-42% thymine,
thereby increasing transcription of the target gene sequence in the human cell.

2. The method of claim 1, the method comprising contacting the human cell with two or more of said fusion proteins.

3. The method of claim 2, wherein at least one of the two or more fusion proteins comprises a VP64 domain, and at least one of the two or more fusion proteins comprises a NF-KB p65 domain.

4. The method of claim 1, wherein the transactivation domain comprises a VP16, VP64 or NF-KB p65 domain.

5. The method of claim 1, wherein the transactivation domain comprises a VP64 domain.

6. The method of claim 1, wherein the transactivation domain comprises a VP16 domain.

7. The method of claim 1, wherein the TALE repeat array has 16.5 to 22.5 repeats.

8. The method of claim 1, wherein the target gene sequence is a sequence of a coding or non-coding gene.

9. The method of claim 8, wherein the non-coding gene is an miRNA gene.

10. The method of claim 1, wherein the regulatory region of the target gene sequence is a promoter region.

11. The method of claim 2, wherein the transactivation domain of the two or more fusion proteins comprises a VP16, VP64 or NF-KB p65 domain.

12. The method of claim 2, wherein the TALE repeat array of the two or more fusion proteins has 16.5 to 22.5 repeats.

13. The method of claim 2, wherein the target gene sequence is a sequence of a coding or non-coding gene.

14. The method of claim 13, wherein the non-coding gene is an miRNA gene.

15. The method of claim 2, wherein the regulatory region of the target gene sequence is a promoter region.

16. A method of increasing transcription of a target gene sequence in a human cell, the method comprising
contacting the human cell with a fusion protein, wherein the fusion protein comprises
a DNA-binding domain comprising a transcription activator-like effector (TALE) repeat array that binds specifically to a subsequence of the target gene sequence, and a transactivation domain that increases transcription of the target gene sequence, wherein the subsequence is within a DNase I hypersensitive region of a regulatory region of the target gene sequence;
wherein the subsequence is 18-24 nucleotides long;
wherein the first nucleotide of the subsequence is a thymine;
wherein the second nucleotide of the subsequence is adenine;
wherein the last nucleotide of the subsequence is a thymine; and
wherein the base composition percentage of the subsequence is other than 0-63% adenine, 11-63% cytosine, 0-25% guanine, or 2-42% thymine,
thereby increasing transcription of the target gene sequence in the human cell.

17. A method of increasing transcription of a target gene sequence in a human cell, the method comprising
contacting the human cell with a fusion protein, wherein the fusion protein comprises
a DNA-binding domain comprising a transcription activator-like effector (TALE) repeat array that binds specifically to a subsequence of the target gene sequence, and a transactivation domain that increases transcription of the target gene sequence, wherein the subsequence is within a DNase I hypersensitive region of a regulatory region of the target gene sequence;
wherein the subsequence is 18-24 nucleotides long;
wherein the first nucleotide of the subsequence is a thymine; and
wherein the base composition percentage of the subsequence is other than 0-63% adenine, 11-63% cytosine, or 2-42% thymine, thereby increasing transcription of the target gene sequence in the human cell.

18. The method of claim 17, wherein the second nucleotide of the subsequence is an adenine.

19. The method of claim 17, wherein the last nucleotide of the subsequence is a thymine.

20. The method of claim 18, wherein the last nucleotide of the subsequence is a thymine.

* * * * *

SEQUENCE LISTING

<160> NUMBER OF SEQ ID NOS: 127

<210> SEQ ID NO 1

```
<211> LENGTH: 19
<212> TYPE: DNA
<213> ORGANISM: Artificial Sequence
<220> FEATURE:
<223> OTHER INFORMATION: binding site sequences

<400> SEQUENCE: 1
tggagccatc tggccgggt                                                    19

<210> SEQ ID NO 2
<211> LENGTH: 14
<212> TYPE: DNA
<213> ORGANISM: Artificial Sequence
<220> FEATURE:
<223> OTHER INFORMATION: binding site sequences

<400> SEQUENCE: 2
tttattccct gaca                                                         14

<210> SEQ ID NO 3
<211> LENGTH: 14
<212> TYPE: DNA
<213> ORGANISM: Artificial Sequence
<220> FEATURE:
<223> OTHER INFORMATION: binding site sequences

<400> SEQUENCE: 3
ttcttactta taac                                                         14

<210> SEQ ID NO 4
<211> LENGTH: 14
<212> TYPE: DNA
<213> ORGANISM: Artificial Sequence
<220> FEATURE:
<223> OTHER INFORMATION: binding site sequences

<400> SEQUENCE: 4
ttctcccacc ccca                                                         14

<210> SEQ ID NO 5
<211> LENGTH: 14
<212> TYPE: DNA
<213> ORGANISM: Artificial Sequence
<220> FEATURE:
<223> OTHER INFORMATION: binding site sequences

<400> SEQUENCE: 5
tcccgagtcc ccaa                                                         14

<210> SEQ ID NO 6
<211> LENGTH: 19
<212> TYPE: DNA
<213> ORGANISM: Artificial Sequence
<220> FEATURE:
<223> OTHER INFORMATION: binding site sequences

<400> SEQUENCE: 6
tacttggagg cagtcaagt                                                    19

<210> SEQ ID NO 7
<211> LENGTH: 21
<212> TYPE: DNA
<213> ORGANISM: Artificial Sequence
<220> FEATURE:
<223> OTHER INFORMATION: binding site sequences

<400> SEQUENCE: 7
```
tggaaagtgg cccagaagca t                                              21

<210> SEQ ID NO 8
<211> LENGTH: 19
<212> TYPE: DNA
<213> ORGANISM: Artificial Sequence
<220> FEATURE:
<223> OTHER INFORMATION: binding site sequences

<400> SEQUENCE: 8
tctcatataa ataggccat                                                 19

<210> SEQ ID NO 9
<211> LENGTH: 14
<212> TYPE: DNA
<213> ORGANISM: Artificial Sequence
<220> FEATURE:
<223> OTHER INFORMATION: binding site sequences

<400> SEQUENCE: 9
tcccttgggt cagg                                                      14

<210> SEQ ID NO 10
<211> LENGTH: 14
<212> TYPE: DNA
<213> ORGANISM: Artificial Sequence
<220> FEATURE:
<223> OTHER INFORMATION: binding site sequences

<400> SEQUENCE: 10
tggttgcact ccgt                                                      14

<210> SEQ ID NO 11
<211> LENGTH: 14
<212> TYPE: DNA
<213> ORGANISM: Artificial Sequence
<220> FEATURE:
<223> OTHER INFORMATION: binding site sequences

<400> SEQUENCE: 11
tgctttgcac aaag                                                      14

<210> SEQ ID NO 12
<211> LENGTH: 14
<212> TYPE: DNA
<213> ORGANISM: Artificial Sequence
<220> FEATURE:
<223> OTHER INFORMATION: binding site sequences

<400> SEQUENCE: 12
tgcacgaata gtgc                                                      14

<210> SEQ ID NO 13
<211> LENGTH: 14
<212> TYPE: DNA
<213> ORGANISM: Artificial Sequence
<220> FEATURE:
<223> OTHER INFORMATION: binding site sequences

<400> SEQUENCE: 13
tagtgctaag ctgg                                                      14

<210> SEQ ID NO 14
<211> LENGTH: 14
<212> TYPE: DNA

```
<213> ORGANISM: Artificial Sequence
<220> FEATURE:
<223> OTHER INFORMATION: binding site sequences

<400> SEQUENCE: 14
tcctgaggtc taac                                                        14

<210> SEQ ID NO 15
<211> LENGTH: 14
<212> TYPE: DNA
<213> ORGANISM: Artificial Sequence
<220> FEATURE:
<223> OTHER INFORMATION: binding site sequences

<400> SEQUENCE: 15
tgaggtctaa cctc                                                        14

<210> SEQ ID NO 16
<211> LENGTH: 20
<212> TYPE: DNA
<213> ORGANISM: Artificial Sequence
<220> FEATURE:
<223> OTHER INFORMATION: binding site sequences

<400> SEQUENCE: 16
tcctccccac ctttaatttt                                                  20

<210> SEQ ID NO 17
<211> LENGTH: 20
<212> TYPE: DNA
<213> ORGANISM: Artificial Sequence
<220> FEATURE:
<223> OTHER INFORMATION: binding site sequences

<400> SEQUENCE: 17
taccatatcc catccaactc                                                  20

<210> SEQ ID NO 18
<211> LENGTH: 18
<212> TYPE: DNA
<213> ORGANISM: Artificial Sequence
<220> FEATURE:
<223> OTHER INFORMATION: binding site sequences

<400> SEQUENCE: 18
tctcctcgtc agaagtct                                                    18

<210> SEQ ID NO 19
<211> LENGTH: 18
<212> TYPE: DNA
<213> ORGANISM: Artificial Sequence
<220> FEATURE:
<223> OTHER INFORMATION: binding site sequences

<400> SEQUENCE: 19
tcggcccctg ccggccca                                                    18

<210> SEQ ID NO 20
<211> LENGTH: 18
<212> TYPE: DNA
<213> ORGANISM: Artificial Sequence
<220> FEATURE:
<223> OTHER INFORMATION: binding site sequences

<400> SEQUENCE: 20
tcggcccctg ccggccca                                                    18
```

```
<210> SEQ ID NO 21
<211> LENGTH: 18
<212> TYPE: DNA
<213> ORGANISM: Artificial Sequence
<220> FEATURE:
<223> OTHER INFORMATION: binding site sequences

<400> SEQUENCE: 21 tcggccctg ccggccca                                                    18

<210> SEQ ID NO 22
<211> LENGTH: 18
<212> TYPE: DNA
<213> ORGANISM: Artificial Sequence
<220> FEATURE:
<223> OTHER INFORMATION: binding site sequences

<400> SEQUENCE: 22 tcggccctg ccggccca                                                    18

<210> SEQ ID NO 23
<211> LENGTH: 18
<212> TYPE: DNA
<213> ORGANISM: Artificial Sequence
<220> FEATURE:
<223> OTHER INFORMATION: binding site sequences

<400> SEQUENCE: 23
tggtagacct tagggcta                                                   18

<210> SEQ ID NO 24
<211> LENGTH: 18
<212> TYPE: DNA
<213> ORGANISM: Artificial Sequence
<220> FEATURE:
<223> OTHER INFORMATION: binding site sequences

<400> SEQUENCE: 24
tggtagacct tagggcta                                                   18

<210> SEQ ID NO 25
<211> LENGTH: 18
<212> TYPE: DNA
<213> ORGANISM: Artificial Sequence
<220> FEATURE:
<223> OTHER INFORMATION: binding site sequences

<400> SEQUENCE: 25
tggtagacct tagggcta                                                   18

<210> SEQ ID NO 26
<211> LENGTH: 18
<212> TYPE: DNA
<213> ORGANISM: Artificial Sequence
<220> FEATURE:
<223> OTHER INFORMATION: binding site sequences

<400> SEQUENCE: 26
tggtagacct tagggcta                                                   18

<210> SEQ ID NO 27
<211> LENGTH: 19
<212> TYPE: DNA
<213> ORGANISM: Artificial Sequence
<220> FEATURE:
```

<223> OTHER INFORMATION: binding site sequences

<400> SEQUENCE: 27
tcccaccccc acagctctg                                              19

<210> SEQ ID NO 28

<400> SEQUENCE: 28

000

<210> SEQ ID NO 29
<211> LENGTH: 15
<212> TYPE: DNA
<213> ORGANISM: Artificial Sequence
<220> FEATURE:
<223> OTHER INFORMATION: binding site sequences

<400> SEQUENCE: 29
tgtaaacctg accct                                                  15

<210> SEQ ID NO 30
<211> LENGTH: 19
<212> TYPE: DNA
<213> ORGANISM: Artificial Sequence
<220> FEATURE:
<223> OTHER INFORMATION: binding site sequences

<400> SEQUENCE: 30
cggagccatc tggccgggt                                              19

<210> SEQ ID NO 31
<211> LENGTH: 14
<212> TYPE: DNA
<213> ORGANISM: Artificial Sequence
<220> FEATURE:
<223> OTHER INFORMATION: binding site sequences

<400> SEQUENCE: 31
tttattccct gaca                                                   14

<210> SEQ ID NO 32
<211> LENGTH: 14
<212> TYPE: DNA
<213> ORGANISM: Artificial Sequence
<220> FEATURE:
<223> OTHER INFORMATION: binding site sequences

<400> SEQUENCE: 32
ttcttactta taac                                                   14

<210> SEQ ID NO 33
<211> LENGTH: 14
<212> TYPE: DNA
<213> ORGANISM: Artificial Sequence
<220> FEATURE:
<223> OTHER INFORMATION: binding site sequences

<400> SEQUENCE: 33
tcccgagtcc ccaa                                                   14

<210> SEQ ID NO 34
<211> LENGTH: 14
<212> TYPE: DNA
<213> ORGANISM: Artificial Sequence
<220> FEATURE:

```
<223> OTHER INFORMATION: binding site sequences

<400> SEQUENCE: 34
ttctcccacc ccca                                                         14

<210> SEQ ID NO 35
<211> LENGTH: 19
<212> TYPE: DNA
<213> ORGANISM: Artificial Sequence
<220> FEATURE:
<223> OTHER INFORMATION: binding site sequences

<400> SEQUENCE: 35
tacttggagg cagtcaagt                                                    19

<210> SEQ ID NO 36
<211> LENGTH: 21
<212> TYPE: DNA
<213> ORGANISM: Artificial Sequence
<220> FEATURE:
<223> OTHER INFORMATION: binding site sequences

<400> SEQUENCE: 36
tggaaagtgg cccagaagca t                                                 21

<210> SEQ ID NO 37
<211> LENGTH: 19
<212> TYPE: DNA
<213> ORGANISM: Artificial Sequence
<220> FEATURE:
<223> OTHER INFORMATION: binding site sequences

<400> SEQUENCE: 37
tctcatataa ataggccat                                                    19

<210> SEQ ID NO 38
<211> LENGTH: 15
<212> TYPE: DNA
<213> ORGANISM: Artificial Sequence
<220> FEATURE:
<223> OTHER INFORMATION: binding site sequences

<400> SEQUENCE: 38
ctcccttggg tcagg                                                        15

<210> SEQ ID NO 39
<211> LENGTH: 15
<212> TYPE: DNA
<213> ORGANISM: Artificial Sequence
<220> FEATURE:
<223> OTHER INFORMATION: binding site sequences

<400> SEQUENCE: 39
ctggttgcac tccgt                                                        15

<210> SEQ ID NO 40
<211> LENGTH: 15
<212> TYPE: DNA
<213> ORGANISM: Artificial Sequence
<220> FEATURE:
<223> OTHER INFORMATION: binding site sequences

<400> SEQUENCE: 40
gtgctttgca caaag                                                        15
```

```
<210> SEQ ID NO 41
<211> LENGTH: 15
<212> TYPE: DNA
<213> ORGANISM: Artificial Sequence
<220> FEATURE:
<223> OTHER INFORMATION: binding site sequences

<400> SEQUENCE: 41
atgcacgaat agtgc                                                       15

<210> SEQ ID NO 42
<211> LENGTH: 15
<212> TYPE: DNA
<213> ORGANISM: Artificial Sequence
<220> FEATURE:
<223> OTHER INFORMATION: binding site sequences

<400> SEQUENCE: 42
atagtgctaa gctgg                                                       15

<210> SEQ ID NO 43
<211> LENGTH: 15
<212> TYPE: DNA
<213> ORGANISM: Artificial Sequence
<220> FEATURE:
<223> OTHER INFORMATION: binding site sequences

<400> SEQUENCE: 43
ttcctgaggt ctaac                                                       15

<210> SEQ ID NO 44
<211> LENGTH: 15
<212> TYPE: DNA
<213> ORGANISM: Artificial Sequence
<220> FEATURE:
<223> OTHER INFORMATION: binding site sequences

<400> SEQUENCE: 44
ctgaggtcta acctc                                                       15

<210> SEQ ID NO 45
<211> LENGTH: 20
<212> TYPE: DNA
<213> ORGANISM: Artificial Sequence
<220> FEATURE:
<223> OTHER INFORMATION: binding site sequences

<400> SEQUENCE: 45
tcctccccac ctttaatttt                                                  20

<210> SEQ ID NO 46
<211> LENGTH: 20
<212> TYPE: DNA
<213> ORGANISM: Artificial Sequence
<220> FEATURE:
<223> OTHER INFORMATION: binding site sequences

<400> SEQUENCE: 46
taccatatcc catccaactc                                                  20

<210> SEQ ID NO 47
<211> LENGTH: 18
<212> TYPE: DNA
<213> ORGANISM: Artificial Sequence
<220> FEATURE:
<223> OTHER INFORMATION: binding site sequences
```

```
<400> SEQUENCE: 47
tctcctcgtc agaagtct                                              18

<210> SEQ ID NO 48
<211> LENGTH: 18
<212> TYPE: DNA
<213> ORGANISM: Artificial Sequence
<220> FEATURE:
<223> OTHER INFORMATION: binding site sequences

<400> SEQUENCE: 48
tcggcccctg ccggccca                                              18

<210> SEQ ID NO 49
<211> LENGTH: 18
<212> TYPE: DNA
<213> ORGANISM: Artificial Sequence
<220> FEATURE:
<223> OTHER INFORMATION: binding site sequences

<400> SEQUENCE: 49
tggtagacct tagggcta                                              18

<210> SEQ ID NO 50
<211> LENGTH: 19
<212> TYPE: DNA
<213> ORGANISM: Artificial Sequence
<220> FEATURE:
<223> OTHER INFORMATION: binding site sequences

<400> SEQUENCE: 50 tcccacccc acagctctg                                              19

<210> SEQ ID NO 51
<211> LENGTH: 15
<212> TYPE: DNA
<213> ORGANISM: Artificial Sequence
<220> FEATURE:
<223> OTHER INFORMATION: binding site sequences

<400> SEQUENCE: 51
tgtaaacctg accct                                                 15

<210> SEQ ID NO 52
<211> LENGTH: 26
<212> TYPE: DNA
<213> ORGANISM: Artificial Sequence
<220> FEATURE:
<223> OTHER INFORMATION: PCR primers

<400> SEQUENCE: 52
gataaacact ggaactctca gtgcaa                                     26

<210> SEQ ID NO 53
<211> LENGTH: 21
<212> TYPE: DNA
<213> ORGANISM: Artificial Sequence
<220> FEATURE:
<223> OTHER INFORMATION: PCR primers

<400> SEQUENCE: 53
gccagcccac gagtttattg t                                          21

<210> SEQ ID NO 54
<211> LENGTH: 29
```

```
<212> TYPE: DNA
<213> ORGANISM: Artificial Sequence
<220> FEATURE:
<223> OTHER INFORMATION: PCR primers

<400> SEQUENCE: 54
caaacctacg tccgagcact gacttcaga                                    29

<210> SEQ ID NO 55
<211> LENGTH: 21
<212> TYPE: DNA
<213> ORGANISM: Artificial Sequence
<220> FEATURE:
<223> OTHER INFORMATION: PCR primers

<400> SEQUENCE: 55
ccatgttcgt catgggtgtg a                                            21

<210> SEQ ID NO 56
<211> LENGTH: 20
<212> TYPE: DNA
<213> ORGANISM: Artificial Sequence
<220> FEATURE:
<223> OTHER INFORMATION: PCR primers

<400> SEQUENCE: 56
catggactgt ggtcatgagt                                              20

<210> SEQ ID NO 57
<211> LENGTH: 24
<212> TYPE: DNA
<213> ORGANISM: Artificial Sequence
<220> FEATURE:
<223> OTHER INFORMATION: PCR primers

<400> SEQUENCE: 57
tcctgcacca ccaactgctt agca                                         24

<210> SEQ ID NO 58
<211> LENGTH: 18
<212> TYPE: DNA
<213> ORGANISM: Artificial Sequence
<220> FEATURE:
<223> OTHER INFORMATION: binding site sequences

<400> SEQUENCE: 58
tcgggaggcg cagcggtt                                                18

<210> SEQ ID NO 59
<211> LENGTH: 18
<212> TYPE: DNA
<213> ORGANISM: Artificial Sequence
<220> FEATURE:
<223> OTHER INFORMATION: binding site sequences

<400> SEQUENCE: 59
ttggggcagc cgggtagc                                                18

<210> SEQ ID NO 60
<211> LENGTH: 18
<212> TYPE: DNA
<213> ORGANISM: Artificial Sequence
<220> FEATURE:
<223> OTHER INFORMATION: binding site sequences

<400> SEQUENCE: 60
``` tggaggggt cggggctc                                                18

<210> SEQ ID NO 61
<211> LENGTH: 19
<212> TYPE: DNA
<213> ORGANISM: Artificial Sequence
<220> FEATURE:
<223> OTHER INFORMATION: binding site sequences

<400> SEQUENCE: 61
tgagtgacct gcttttggg                                              19

<210> SEQ ID NO 62
<211> LENGTH: 19
<212> TYPE: DNA
<213> ORGANISM: Artificial Sequence
<220> FEATURE:
<223> OTHER INFORMATION: binding site sequences

<400> SEQUENCE: 62
tgagtgagtg tgtgcgtgt                                              19

<210> SEQ ID NO 63
<211> LENGTH: 19
<212> TYPE: DNA
<213> ORGANISM: Artificial Sequence
<220> FEATURE:
<223> OTHER INFORMATION: binding site sequences

<400> SEQUENCE: 63
tcactccagg attccaata                                              19

<210> SEQ ID NO 64
<211> LENGTH: 18
<212> TYPE: DNA
<213> ORGANISM: Artificial Sequence
<220> FEATURE:
<223> OTHER INFORMATION: binding site sequences

<400> SEQUENCE: 64
ttctgttcac gggactca                                               18

<210> SEQ ID NO 65
<211> LENGTH: 18
<212> TYPE: DNA
<213> ORGANISM: Artificial Sequence
<220> FEATURE:
<223> OTHER INFORMATION: binding site sequences

<400> SEQUENCE: 65
tccgaacagc tccgcgca                                               18

<210> SEQ ID NO 66
<211> LENGTH: 18
<212> TYPE: DNA
<213> ORGANISM: Artificial Sequence
<220> FEATURE:
<223> OTHER INFORMATION: binding site sequences

<400> SEQUENCE: 66
ttcccctgct gggtagtg                                               18

<210> SEQ ID NO 67
<211> LENGTH: 18
<212> TYPE: DNA
<213> ORGANISM: Artificial Sequence

```
<220> FEATURE:
<223> OTHER INFORMATION: binding site sequences

<400> SEQUENCE: 67
tacgcctcag acctgatc                                                 18

<210> SEQ ID NO 68
<211> LENGTH: 18
<212> TYPE: DNA
<213> ORGANISM: Artificial Sequence
<220> FEATURE:
<223> OTHER INFORMATION: binding site sequences

<400> SEQUENCE: 68
tccctcaatc tgggaaag                                                 18

<210> SEQ ID NO 69
<211> LENGTH: 18
<212> TYPE: DNA
<213> ORGANISM: Artificial Sequence
<220> FEATURE:
<223> OTHER INFORMATION: binding site sequences

<400> SEQUENCE: 69
tggaagcaat ctatttat                                                 18

<210> SEQ ID NO 70
<211> LENGTH: 18
<212> TYPE: DNA
<213> ORGANISM: Artificial Sequence
<220> FEATURE:
<223> OTHER INFORMATION: binding site sequences

<400> SEQUENCE: 70
tacatttaac atgtagat                                                 18

<210> SEQ ID NO 71
<211> LENGTH: 18
<212> TYPE: DNA
<213> ORGANISM: Artificial Sequence
<220> FEATURE:
<223> OTHER INFORMATION: binding site sequences

<400> SEQUENCE: 71
tagaaacaca atgccttt                                                 18

<210> SEQ ID NO 72
<211> LENGTH: 18
<212> TYPE: DNA
<213> ORGANISM: Artificial Sequence
<220> FEATURE:
<223> OTHER INFORMATION: binding site sequences

<400> SEQUENCE: 72
tgggagcact cattgtta                                                 18

<210> SEQ ID NO 73
<211> LENGTH: 18
<212> TYPE: DNA
<213> ORGANISM: Artificial Sequence
<220> FEATURE:
<223> OTHER INFORMATION: binding site sequences

<400> SEQUENCE: 73
taatctatgc catcaaac                                                 18
```

```
<210> SEQ ID NO 74
<211> LENGTH: 16
<212> TYPE: DNA
<213> ORGANISM: Artificial Sequence
<220> FEATURE:
<223> OTHER INFORMATION: binding site sequences

<400> SEQUENCE: 74
ttgggggtga ccgccg                                                   16

<210> SEQ ID NO 75
<211> LENGTH: 18
<212> TYPE: DNA
<213> ORGANISM: Artificial Sequence
<220> FEATURE:
<223> OTHER INFORMATION: binding site sequences

<400> SEQUENCE: 75
ttgggggtga ccgccgga                                                 18

<210> SEQ ID NO 76
<211> LENGTH: 20
<212> TYPE: DNA
<213> ORGANISM: Artificial Sequence
<220> FEATURE:
<223> OTHER INFORMATION: binding site sequences

<400> SEQUENCE: 76
ttgggggtga ccgccggagc                                               20

<210> SEQ ID NO 77
<211> LENGTH: 22
<212> TYPE: DNA
<213> ORGANISM: Artificial Sequence
<220> FEATURE:
<223> OTHER INFORMATION: binding site sequences

<400> SEQUENCE: 77
ttgggggtga ccgccggagc gc                                            22

<210> SEQ ID NO 78
<211> LENGTH: 24
<212> TYPE: DNA
<213> ORGANISM: Artificial Sequence
<220> FEATURE:
<223> OTHER INFORMATION: binding site sequences

<400> SEQUENCE: 78
ttgggggtga ccgccggagc gcgg                                          24

<210> SEQ ID NO 79
<211> LENGTH: 26
<212> TYPE: DNA
<213> ORGANISM: Artificial Sequence
<220> FEATURE:
<223> OTHER INFORMATION: binding site sequences

<400> SEQUENCE: 79
ttgggggtga ccgccggagc gcggcg                                        26

<210> SEQ ID NO 80
<211> LENGTH: 16
<212> TYPE: DNA
<213> ORGANISM: Artificial Sequence
<220> FEATURE:
<223> OTHER INFORMATION: binding site sequences
```

```
<400> SEQUENCE: 80
tcccgcagct gaccag                                                      16

<210> SEQ ID NO 81
<211> LENGTH: 18
<212> TYPE: DNA
<213> ORGANISM: Artificial Sequence
<220> FEATURE:
<223> OTHER INFORMATION: binding site sequences

<400> SEQUENCE: 81
tcccgcagct gaccagtc                                                    18

<210> SEQ ID NO 82
<211> LENGTH: 20
<212> TYPE: DNA
<213> ORGANISM: Artificial Sequence
<220> FEATURE:
<223> OTHER INFORMATION: binding site sequences

<400> SEQUENCE: 82
tcccgcagct gaccagtcgc                                                  20

<210> SEQ ID NO 83
<211> LENGTH: 22
<212> TYPE: DNA
<213> ORGANISM: Artificial Sequence
<220> FEATURE:
<223> OTHER INFORMATION: binding site sequences

<400> SEQUENCE: 83
tcccgcagct gaccagtcgc gc                                               22

<210> SEQ ID NO 84
<211> LENGTH: 24
<212> TYPE: DNA
<213> ORGANISM: Artificial Sequence
<220> FEATURE:
<223> OTHER INFORMATION: binding site sequences

<400> SEQUENCE: 84
tcccgcagct gaccagtcgc gctg                                             24

<210> SEQ ID NO 85
<211> LENGTH: 26
<212> TYPE: DNA
<213> ORGANISM: Artificial Sequence
<220> FEATURE:
<223> OTHER INFORMATION: binding site sequences

<400> SEQUENCE: 85
tcccgcagct gaccagtcgc gctgac                                           26

<210> SEQ ID NO 86
<211> LENGTH: 16
<212> TYPE: DNA
<213> ORGANISM: Artificial Sequence
<220> FEATURE:
<223> OTHER INFORMATION: binding site sequences

<400> SEQUENCE: 86
taccacctcc tcccg                                                       16

<210> SEQ ID NO 87
```

```
<210> SEQ ID NO 87
<211> LENGTH: 18
<212> TYPE: DNA
<213> ORGANISM: Artificial Sequence
<220> FEATURE:
<223> OTHER INFORMATION: binding site sequences

<400> SEQUENCE: 87
taccacctcc tccccggc                                            18

<210> SEQ ID NO 88
<211> LENGTH: 20
<212> TYPE: DNA
<213> ORGANISM: Artificial Sequence
<220> FEATURE:
<223> OTHER INFORMATION: binding site sequences

<400> SEQUENCE: 88
taccacctcc tccccggccg                                          20

<210> SEQ ID NO 89
<211> LENGTH: 22
<212> TYPE: DNA
<213> ORGANISM: Artificial Sequence
<220> FEATURE:
<223> OTHER INFORMATION: binding site sequences

<400> SEQUENCE: 89
taccacctcc tccccggccg gc                                       22

<210> SEQ ID NO 90
<211> LENGTH: 24
<212> TYPE: DNA
<213> ORGANISM: Artificial Sequence
<220> FEATURE:
<223> OTHER INFORMATION: binding site sequences

<400> SEQUENCE: 90
taccacctcc tccccggccg gcgg                                     24

<210> SEQ ID NO 91
<211> LENGTH: 26
<212> TYPE: DNA
<213> ORGANISM: Artificial Sequence
<220> FEATURE:
<223> OTHER INFORMATION: binding site sequences

<400> SEQUENCE: 91
taccacctcc tccccggccg gcggcg                                   26

<210> SEQ ID NO 92
<211> LENGTH: 16
<212> TYPE: DNA
<213> ORGANISM: Artificial Sequence
<220> FEATURE:
<223> OTHER INFORMATION: binding site sequences

<400> SEQUENCE: 92
tccccggccg gcggcg                                              16

<210> SEQ ID NO 93
<211> LENGTH: 18
<212> TYPE: DNA
<213> ORGANISM: Artificial Sequence
<220> FEATURE:
<223> OTHER INFORMATION: binding site sequences

<400> SEQUENCE: 93
```
tccccggccg gcggcgga                                                  18

<210> SEQ ID NO 94
<211> LENGTH: 20
<212> TYPE: DNA
<213> ORGANISM: Artificial Sequence
<220> FEATURE:
<223> OTHER INFORMATION: binding site sequences

<400> SEQUENCE: 94
tccccggccg gcggcggaca                                                20

<210> SEQ ID NO 95
<211> LENGTH: 22
<212> TYPE: DNA
<213> ORGANISM: Artificial Sequence
<220> FEATURE:
<223> OTHER INFORMATION: binding site sequences

<400> SEQUENCE: 95
tccccggccg gcggcggaca gt                                             22

<210> SEQ ID NO 96
<211> LENGTH: 24
<212> TYPE: DNA
<213> ORGANISM: Artificial Sequence
<220> FEATURE:
<223> OTHER INFORMATION: binding site sequences

<400> SEQUENCE: 96
tccccggccg gcggcggaca gtgg                                           24

<210> SEQ ID NO 97
<211> LENGTH: 26
<212> TYPE: DNA
<213> ORGANISM: Artificial Sequence
<220> FEATURE:
<223> OTHER INFORMATION: binding site sequences

<400> SEQUENCE: 97
tccccggccg gcggcggaca gtggac                                         26

<210> SEQ ID NO 98
<211> LENGTH: 16
<212> TYPE: DNA
<213> ORGANISM: Artificial Sequence
<220> FEATURE:
<223> OTHER INFORMATION: binding site sequences

<400> SEQUENCE: 98
tggacgcggc ggcgag                                                    16

<210> SEQ ID NO 99
<211> LENGTH: 18
<212> TYPE: DNA
<213> ORGANISM: Artificial Sequence
<220> FEATURE:
<223> OTHER INFORMATION: binding site sequences

<400> SEQUENCE: 99
tggacgcggc ggcgagcc                                                  18

<210> SEQ ID NO 100
<211> LENGTH: 20
<212> TYPE: DNA

```
<213> ORGANISM: Artificial Sequence
<220> FEATURE:
<223> OTHER INFORMATION: binding site sequences

<400> SEQUENCE: 100
tggacgcggc ggcgagccgc                                                   20

<210> SEQ ID NO 101
<211> LENGTH: 22
<212> TYPE: DNA
<213> ORGANISM: Artificial Sequence
<220> FEATURE:
<223> OTHER INFORMATION: binding site sequences

<400> SEQUENCE: 101
tggacgcggc ggcgagccgc gg                                                22

<210> SEQ ID NO 102
<211> LENGTH: 24
<212> TYPE: DNA
<213> ORGANISM: Artificial Sequence
<220> FEATURE:
<223> OTHER INFORMATION: binding site sequences

<400> SEQUENCE: 102
tggacgcggc ggcgagccgc gggc                                              24

<210> SEQ ID NO 103
<211> LENGTH: 26
<212> TYPE: DNA
<213> ORGANISM: Artificial Sequence
<220> FEATURE:
<223> OTHER INFORMATION: binding site sequences

<400> SEQUENCE: 103
tggacgcggc ggcgagccgc gggcag                                            26

<210> SEQ ID NO 104
<211> LENGTH: 16
<212> TYPE: DNA
<213> ORGANISM: Artificial Sequence
<220> FEATURE:
<223> OTHER INFORMATION: binding site sequences

<400> SEQUENCE: 104
tcccaagggg gagggc                                                       16

<210> SEQ ID NO 105
<211> LENGTH: 18
<212> TYPE: DNA
<213> ORGANISM: Artificial Sequence
<220> FEATURE:
<223> OTHER INFORMATION: binding site sequences

<400> SEQUENCE: 105
tcccaagggg gagggctc                                                     18

<210> SEQ ID NO 106
<211> LENGTH: 20
<212> TYPE: DNA
<213> ORGANISM: Artificial Sequence
<220> FEATURE:
<223> OTHER INFORMATION: binding site sequences

<400> SEQUENCE: 106
tcccaagggg gagggctcac                                                   20
```

<210> SEQ ID NO 107
<211> LENGTH: 22
<212> TYPE: DNA
<213> ORGANISM: Artificial Sequence
<220> FEATURE:
<223> OTHER INFORMATION: binding site sequences

<400> SEQUENCE: 107
tcccaagggg gagggctcac gc                                            22

<210> SEQ ID NO 108
<211> LENGTH: 24
<212> TYPE: DNA
<213> ORGANISM: Artificial Sequence
<220> FEATURE:
<223> OTHER INFORMATION: binding site sequences

<400> SEQUENCE: 108
tcccaagggg gagggctcac gccg                                          24

<210> SEQ ID NO 109
<211> LENGTH: 26
<212> TYPE: DNA
<213> ORGANISM: Artificial Sequence
<220> FEATURE:
<223> OTHER INFORMATION: binding site sequences

<400> SEQUENCE: 109
tcccaagggg gagggctcac gccgcg                                        26

<210> SEQ ID NO 110
<211> LENGTH: 16
<212> TYPE: DNA
<213> ORGANISM: Artificial Sequence
<220> FEATURE:
<223> OTHER INFORMATION: binding site sequences

<400> SEQUENCE: 110
tccgtcagcg cgactg                                                   16

<210> SEQ ID NO 111
<211> LENGTH: 18
<212> TYPE: DNA
<213> ORGANISM: Artificial Sequence
<220> FEATURE:
<223> OTHER INFORMATION: binding site sequences

<400> SEQUENCE: 111
tccgtcagcg cgactggt                                                 18

<210> SEQ ID NO 112
<211> LENGTH: 20
<212> TYPE: DNA
<213> ORGANISM: Artificial Sequence
<220> FEATURE:
<223> OTHER INFORMATION: binding site sequences

<400> SEQUENCE: 112
tccgtcagcg cgactggtca                                               20

<210> SEQ ID NO 113
<211> LENGTH: 22
<212> TYPE: DNA
<213> ORGANISM: Artificial Sequence
<220> FEATURE:

```
<223> OTHER INFORMATION: binding site sequences

<400> SEQUENCE: 113
tccgtcagcg cgactggtca gc                                      22

<210> SEQ ID NO 114
<211> LENGTH: 24
<212> TYPE: DNA
<213> ORGANISM: Artificial Sequence
<220> FEATURE:
<223> OTHER INFORMATION: binding site sequences

<400> SEQUENCE: 114
tccgtcagcg cgactggtca gctg                                    24

<210> SEQ ID NO 115
<211> LENGTH: 26
<212> TYPE: DNA
<213> ORGANISM: Artificial Sequence
<220> FEATURE:
<223> OTHER INFORMATION: binding site sequences

<400> SEQUENCE: 115
tccgtcagcg cgactggtca gctgcg                                  26

<210> SEQ ID NO 116
<211> LENGTH: 16
<212> TYPE: DNA
<213> ORGANISM: Artificial Sequence
<220> FEATURE:
<223> OTHER INFORMATION: binding site sequences

<400> SEQUENCE: 116
tccactgtcc gccgcc                                             16

<210> SEQ ID NO 117
<211> LENGTH: 18
<212> TYPE: DNA
<213> ORGANISM: Artificial Sequence
<220> FEATURE:
<223> OTHER INFORMATION: binding site sequences

<400> SEQUENCE: 117
tccactgtcc gccgccgg                                           18

<210> SEQ ID NO 118
<211> LENGTH: 20
<212> TYPE: DNA
<213> ORGANISM: Artificial Sequence
<220> FEATURE:
<223> OTHER INFORMATION: binding site sequences

<400> SEQUENCE: 118
tccactgtcc gccgccggcc                                         20

<210> SEQ ID NO 119
<211> LENGTH: 22
<212> TYPE: DNA
<213> ORGANISM: Artificial Sequence
<220> FEATURE:
<223> OTHER INFORMATION: binding site sequences

<400> SEQUENCE: 119
tccactgtcc gccgccggcc gg                                      22
```

```
<210> SEQ ID NO 120
<211> LENGTH: 24
<212> TYPE: DNA
<213> ORGANISM: Artificial Sequence
<220> FEATURE:
<223> OTHER INFORMATION: binding site sequences

<400> SEQUENCE: 120
tccactgtcc gccgccggcc gggg                                            24

<210> SEQ ID NO 121
<211> LENGTH: 26
<212> TYPE: DNA
<213> ORGANISM: Artificial Sequence
<220> FEATURE:
<223> OTHER INFORMATION: binding site sequences

<400> SEQUENCE: 121
tccactgtcc gccgccggcc ggggag                                          26

<210> SEQ ID NO 122
<211> LENGTH: 16
<212> TYPE: DNA
<213> ORGANISM: Artificial Sequence
<220> FEATURE:
<223> OTHER INFORMATION: binding site sequences

<400> SEQUENCE: 122
tccaccccgc ctccgg                                                     16

<210> SEQ ID NO 123
<211> LENGTH: 18
<212> TYPE: DNA
<213> ORGANISM: Artificial Sequence
<220> FEATURE:
<223> OTHER INFORMATION: binding site sequences

<400> SEQUENCE: 123
tccaccccgc ctccgggc                                                   18

<210> SEQ ID NO 124
<211> LENGTH: 20
<212> TYPE: DNA
<213> ORGANISM: Artificial Sequence
<220> FEATURE:
<223> OTHER INFORMATION: binding site sequences

<400> SEQUENCE: 124
tccaccccgc ctccgggcgc                                                 20

<210> SEQ ID NO 125
<211> LENGTH: 22
<212> TYPE: DNA
<213> ORGANISM: Artificial Sequence
<220> FEATURE:
<223> OTHER INFORMATION: binding site sequences

<400> SEQUENCE: 125
tccaccccgc ctccgggcgc gg                                              22

<210> SEQ ID NO 126
<211> LENGTH: 24
<212> TYPE: DNA
```

```
<213> ORGANISM: Artificial Sequence
<220> FEATURE:
<223> OTHER INFORMATION: binding site sequences

<400> SEQUENCE: 126
tccaccccgc ctccgggcgc gggc                                          24

<210> SEQ ID NO 127
<211> LENGTH: 26
<212> TYPE: DNA
<213> ORGANISM: Artificial Sequence
<220> FEATURE:
<223> OTHER INFORMATION: binding site sequences

<400> SEQUENCE: 127
tccaccccgc ctccgggcgc gggctc                                        26
```